United States Patent
Kwok et al.

(10) Patent No.: US 10,913,770 B2
(45) Date of Patent: Feb. 9, 2021

(54) MERTANSINE POLYPEPTIDE CONJUGATES

(71) Applicant: Vision Global Holdings Limited, Hong Kong (CN)

(72) Inventors: Sui-Yi Kwok, Hong Kong (CN); Norman Fung-Man Wai, Vancouver (CA); Man-Kin Wong, Hong Kong (CN); Benjamin Chi-Yin Wai, Vancouver (CA)

(73) Assignee: Vision Global Holdings Limited, Hong Kong (CN)

( * ) Notice: Subject to any disclaimer, the term of this patent is extended or adjusted under 35 U.S.C. 154(b) by 0 days.

(21) Appl. No.: 15/931,722

(22) Filed: May 14, 2020

(65) Prior Publication Data

US 2020/0361988 A1    Nov. 19, 2020

Related U.S. Application Data

(60) Provisional application No. 62/847,366, filed on May 14, 2019.

(51) Int. Cl.
*C07K 5/12* (2006.01)
*A61K 38/00* (2006.01)

(52) U.S. Cl.
CPC ............... *C07K 5/12* (2013.01); *A61K 38/00* (2013.01)

(58) Field of Classification Search
CPC .. C07K 5/12; C07K 2/00; A61K 38/00; A61P 35/00
See application file for complete search history.

(56) References Cited

FOREIGN PATENT DOCUMENTS

| WO | WO-2017136581 A1 * | 8/2017 | .............. A61K 47/64 |
| WO | WO-2017180713 A1 * | 10/2017 | .............. A61P 35/00 |
| WO | 2019219002 A1 | 11/2019 | |

OTHER PUBLICATIONS

Fang et al, Angewandte Chemie, International Edition (2016), 55(7), 2416-2420 (Year: 2016).*

* cited by examiner

*Primary Examiner* — Sudhakar Katakam

(57) ABSTRACT

Provided herein are mertansine polypeptide conjugates useful in the treatment of cancer, pharmaceutical compositions comprising the same, and methods of use and preparation thereof. The methods provided herein are highly N-terminal selective and are capable of yielding N-terminal mertansine conjugated polypeptides with site selectivity of 99% or greater.

17 Claims, 19 Drawing Sheets

Specification includes a Sequence Listing.

A
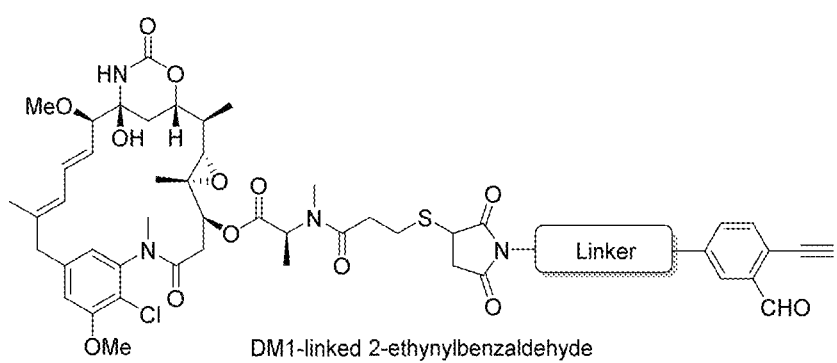
DM1-linked 2-ethynylbenzaldehyde
B
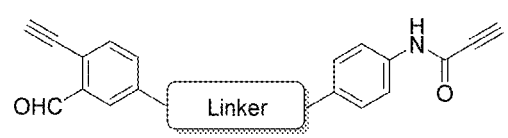
Fluorescein-linked 2-ethynylbenzaldehyde
FIG. 2

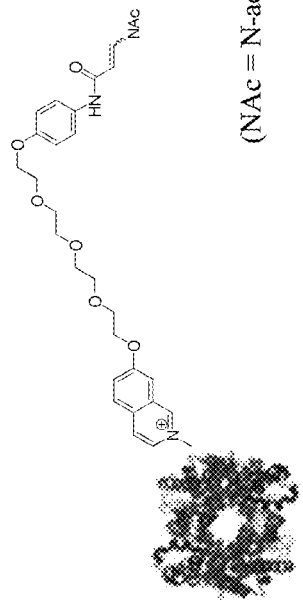
(NAc = N-acetyl cysteine)
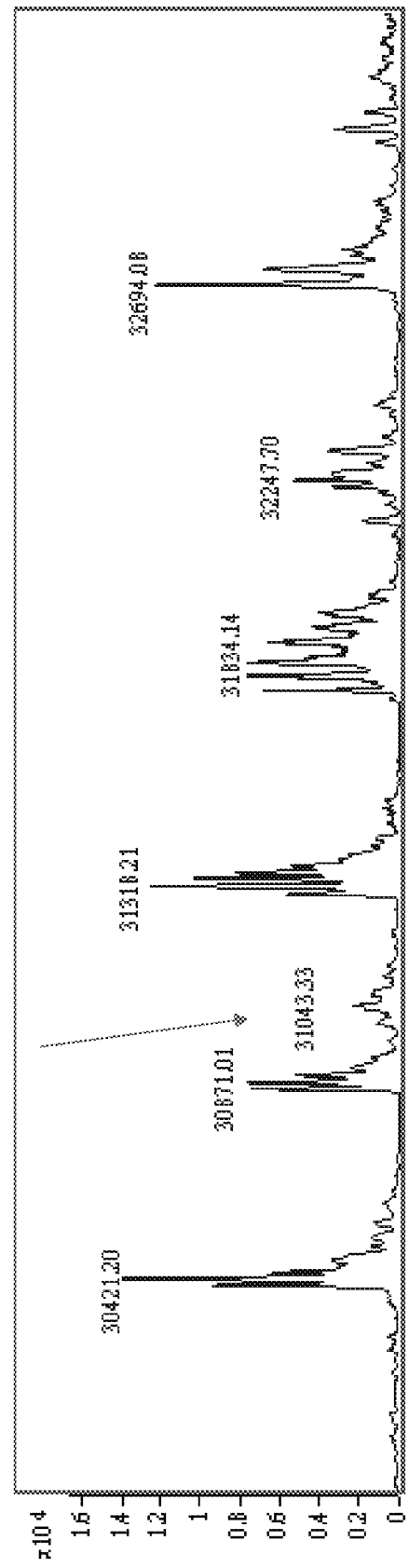
FIG. 3E di-alpha chain (SEQ ID NO: 1)

MLSPADKTNVKAAWGKVGAHAGEYGAEAFERMFLSFPTTKTYFPHFDLSHGSAQVKGQGK

KVADALTNAVAHVDDMPNALSALSDLHAHKLRVDPVNFKLLSHCLLVTLAAHLPAEFTPA

VHASLDKFLASVSTVLTSKYRGMLSPADKTNVKAAWGKVGAHAGEYGAEAFERMFLSFPT

TKTYFPHFDLSHGSAQVKGQGKKVADALTNAVAHVDDMPNALSALSDLHAHKLRVDPVNF

KLLSHCLLVTLAAHLPAEFTPAVHASLDKFLASVSTVLTSKYR beta chain for TBM1 (SEQ ID NO: 2)

MHLTPEEKSAVTALWGKVNVDEVGGEALGRLLVVYPWTQRFFESFGDLSTPDAVMGNPKV

KAHGKKVLGAFSDGLAHLDNLKGTFATLSELHCDKLHVDPENFRLLGNVLVCVLAHHFGK

EFTPPVQAAYQKVVAGVANALAHKYH beta chain for TBM9 (SEQ ID NO: 3)

MHLTPEEKSAVTALWGKVNVDEVGGEALGRLLVVYPWTQRFFESFGDLSTPDAVMGNPKV

KAHGKKVLGAFSDGLAHLDNLDGTFATLSELHCDKLHVDPENFRLLGKVLVCVLAHHFGK

EFTPPVQAAYQKVVAGVANALAHKYH di-alpha chain for TBN (SEQ ID NO: 4)

MLSPADKTNVKAAWGKVGAHAGEYGAEALERMFLSFPTTKTYFPHFDLSHGSAQVKGHGK

KVADALTNAVAHVDDMPNALSALSDLHAHKLRVDPVNFKLLSHCLLVTLAAHLPAEFTPA

VHASLDKFLASVSTVLTSKYRGMLSPADKTNVKAAWGKVGAHAGEYGAEALERMFLSFPT

TKTYFPHFDLSHGSAQVKGHGKKVADALTNAVAHVDDMPNALSALSDLHAHKLRVDPVNF

KLLSHCLLVTLAAHLPAEFTPAVHASLDKFLASVSTVLTSKYR beta chain for TBN (SEQ ID NO: 5)

MHLTPEEKSAVTALWGKVNVDEVGGEALGRLLVVYPWTQRFFESFGDLSTPDAVMGNPKV

KAHGKKVLGAFSDGLAHLDNLKGTFATLSELHCDKLHVDPENFRLLGNVLVCVLAHHFGK

EFTPPVQAAYQKVVAGVANALAHKYH

FIG. 7

MERTANSINE POLYPEPTIDE CONJUGATES

CROSS-REFERENCE TO RELATED APPLICATIONS

This application claims the benefit of priority of U.S. Provisional Application No. 62/847,366, filed on May 14, 2019, the contents of which being hereby incorporated by reference in their entirety for all purposes.

TECHNICAL FIELD

The present disclosure relates to mertansine polypeptide conjugates useful in the treatment of cancer, pharmaceutical compositions comprising the same, and methods of use and preparation thereof.

BACKGROUND

Maytansine was first isolated in 1972 from *Maytenus ovatus* on the basis of its cytotoxicity against KB cells and its antileukemic activity against the mouse P388 lymphocytic leukemia. Maytansine is an antimitotic agent, which acts as an inhibitor of tubulin polymerization, thus interfering with the formation of microtubules in the cell nucleus. Maytansine also inhibits DNA, RNA, and protein synthesis.

While maytansine showed promising results in Phase I clinical trials in patients with acute lymphocytic leukemia, breast carcinoma, ovarian cancer, thymoma, melanoma, and non-small scale lung cancer, dose-limiting toxicity was observed in Phase II clinical trials.

One approach for improving the toxicity and target selectivity of maytansine is conjugating it to a targeting molecule, such as an antibody, which allows delivery of the maytansine to a desired cell type. This approach has resulted in the development of a number of mertansine (a maytansine analog) antibody drug conjugates, such as trastuzumab emtansine, lorvotuzumab mertansine, and cantuzumab mertansine.

Trastuzumab emtansine has been approved for use in the treatment of HER2-positive metastatic breast cancer. Lorvotuzumab mertansine targets CD56 positive cancers and is currently undergoing clinical trials for small-cell lung cancer.

Despite the vast therapeutic potential of mertansine antibody drug conjugates, current approaches for their preparation still suffer from unselective chemical modification, which results in heterogeneous chemical modification of the antibody target. The resulting heterogeneous biotherapeutic agents can lead to analytical complications as well as safety and efficacy concerns.

In view of at least the foregoing challenges, there exists a need to develop improved methods for the selective conjugation of mertansine to targeting molecules, which e.g., reduce product heterogeneity providing a more reliable therapeutic tool with predictable properties and batch-to-batch consistency and that can extend the therapeutic potential of mertansine to other cancer types.

SUMMARY

Provided herein are mertansine polypeptide conjugates, pharmaceutical compositions comprising the same, and methods of use and preparation thereof. The methods provided herein are highly N-terminal selective and are capable of yielding N-terminal mertansine conjugated polypeptides with site selectivity of 99% or greater.

In a first aspect, provided herein is a polypeptide conjugate represented by the structure of Formula 1:

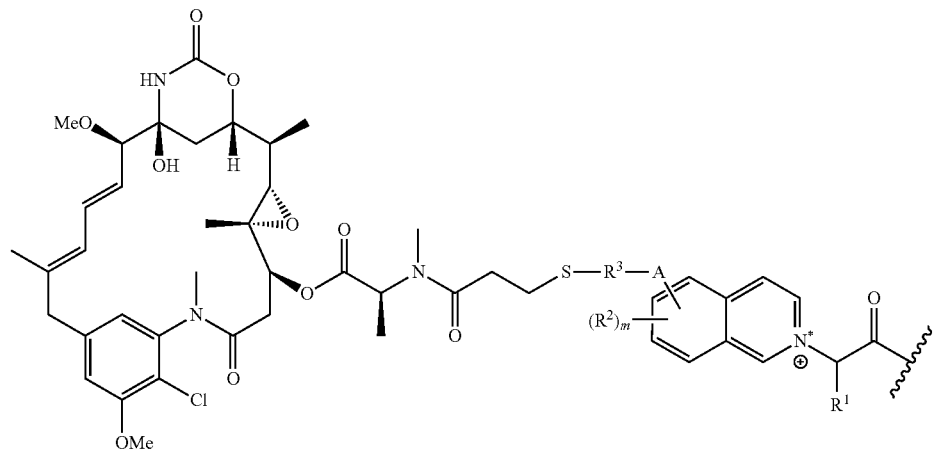

1 or a conjugate salt or zwitterion thereof, wherein
A is a linker or is absent;
m is a whole number selected from 1-3;
N* is the N-terminal nitrogen of the polypeptide conjugate;
$R^1$ is the side chain of the N-terminal amino acid of the polypeptide conjugate;
$R^2$ independently for each instance is selected from the group consisting of hydrogen, alkyl, alkenyl, alkynyl, cycloalkyl, aryl, aralkyl, heterocycloalkyl, heteraryl, halide, cyano, nitro, hydroxyl, $-OR^4$, $-SR^4$, $-(C=O)OR^4$, $-O(C=O)R^4$, $-N(R^4)_2$, $-(C=O)N(R^4)_2$, $-N(R^4)(C=O)R^4$, $-N(R^4)(C=O)N(R^4)_2$, $-SO_2R^4$, $-N(R^4)SO_2R^4$, and $-SO_2N(R^4)_2$;
$R^3$ is selected from the group consisting of:

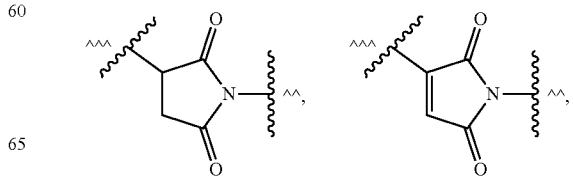

3

-continued

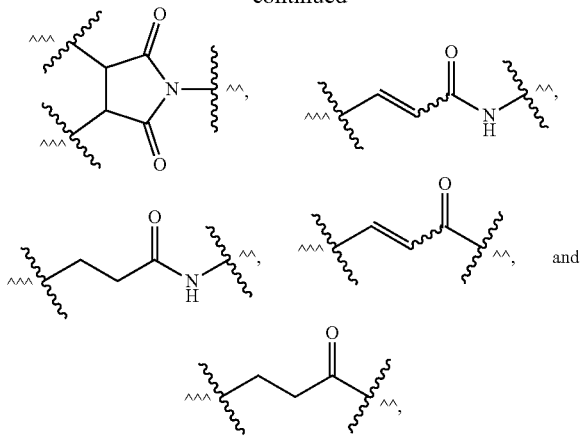

wherein ^^ indicates the position of a covalent bond with A and ^^^ indicates the position of a covalent bond with the moiety:

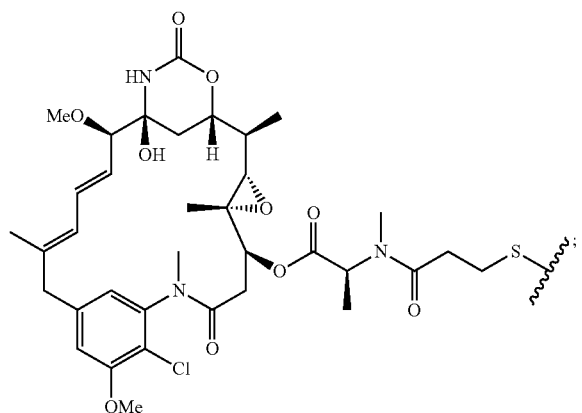

and
$R^4$ for each instance is independently selected from the group consisting of hydrogen, alkyl, alkenyl, alkynyl, cycloalkyl, aryl, aralkyl, heterocycloalkyl, and heteraryl; or two instances of $R^4$ taken together with the atoms to which they are attached form a 5-6 membered heterocycloalkyl.

In a first embodiment of the first aspect, provided herein is the polypeptide conjugate of the first aspect, wherein the polypeptide is a protein, enzyme, antibody, glycoprotein, or lipoprotein.

In a second embodiment of the first aspect, provided herein is the polypeptide conjugate of the first embodiment of the first aspect, wherein the protein is a hemoglobin protein.

In a third embodiment of the first aspect, provided herein is the polypeptide conjugate of the second embodiment of the first aspect, wherein the hemoglobin protein is a hemoglobin tetramer, hemoglobin dimer, or hemoglobin monomer.

In a fourth embodiment of the first aspect, provided herein is the polypeptide conjugate of the third embodiment of the first aspect, wherein the hemoglobin tetramer is a cross-linked hemoglobin tetramer.

In a fifth embodiment of the first aspect, provided herein is the polypeptide conjugate of the first aspect, wherein m is 1 and $R^2$ is hydrogen, —$OR^4$, or halide.

4

In a sixth embodiment of the first aspect, provided herein is the polypeptide conjugate of the first aspect, wherein the linker is absent or selected from the group consisting of —$(CR_2)_n$—*, —$O(CR_2)_n$—*, —$(CR_2)_n$O—*, —$O(CR_2)_nO$—*, —$(CR_2)_nC(=O)$—*, —$C(=O)(CR_2)_n$—*, —$C(=O)O(CR_2)_n$—*, —$(CR_2)_nOC(=O)$—*, —$O(CR_2)_nC(=O)$—*, —$O(CR_2)_nC(=O)N(R)(CR_2)_p$—*, —$O(CR_2)_nN(R)C(=O)N(R)(CR_2)_p$—*, —$O(CR_2)_nC(=O)O(CR_2)_p$—*, —$O(CR_2)_nOC(=O)N(R)(CR_2)_p$—*, —$C(=O)(CR_2)_nO$—*, —$O(CR_2)_nN(R)C(=O)$—*, —$O(CR_2)_nN(R)C(=O)(CR_2)_p$—*, —$C(=O)N(R)(CR_2)_nO$—*, —$OC(=O)(CR_2)_n$—*, —$(CR_2)_nC(=O)O$—*, —$OC(=O)(CR_2)_n$—*, —$(CR_2)_nOC(=O)O$—*, —$C(=O)N(R)(CR_2)_n$—*, —$(CR_2)_n(R)NC(=O)$—*, —$N(R)C(=O)(CR_2)_n$—*, —$(CR_2)_nC(=O)N(R)$—*, —$N(R)C(=O)O(CR_2)_n$—*, —$(CR_2)_nOC(=O)N(R)$—*, —$OC(=O)N(R)(CR_2)_n$—*, —$(CR_2)_nN(R)C(=O)O$—*, —$(OCR_2CR_2)_n$—*, —$(CR_2CR_2O)_n$—*, —$(OCR_2CR_2)_nOAr$—*, —$(OCR_2CR_2)_nAr$—*, —$(OCR_2CR_2)_n(C=O)$—*, —$(OCR_2CR_2)_nO(C=O)$—*, —$(OCR_2CR_2)_nN(R)(C=O)$—*, —$(OCR_2CR_2)_n(C=O)(CR_2)_p$—*, —$(OCR_2CR_2)_nO(C=O)(CR_2)_p$—*, —$(OCR_2CR_2)_nN(R)(C=O)(CR_2)_p$—*, —$(OCR_2CR_2)_n(C=O)O(CR_2)_p$—*, —$(OCR_2CR_2)_nO(C=O)O(CR_2)_p$—*, —$(OCR_2CR_2)_nN(R)(C=O)O(CR_2)_p$—*, —$(OCR_2CR_2)_n(C=O)N(R)(CR_2)_p$—*, —$(OCR_2CR_2)_nO(C=O)N(R)(CR_2)_p$—*, —$(OCR_2CR_2)_nN(R)(C=O)N(R)(CR_2)_p$—*, —$OCR_2(C=O)$—*, —$OCR_2(C=O)(CR_2)_p$—*, —$OCR_2(C=O)O(CR_2)_p$—*, —$OCR_2(C=O)N(R)(CR_2)_p$—*, —$C(=O)O(CR_2CR_2O)_nCR_2CR_2$—*, —$C(=O)N(R)(CR_2CR_2O)_nCR_2CR_2$—*, —$S(CR_2)_n$—*, —$(CR_2)_nS$—*, —$(CR_2)_nSS(CR_2)_p$—*, —$SO_2(CR_2)_n$—*, —$(CR_2)_n$ $SO_2$—*, —$N(R)SO_2(CR_2)_n$—*, —$(CR_2)_nSO_2N(R)$—*, —$SO_2N(R)(CR_2)_n$—*, —$(CR_2)_nN(R)SO_2$—*, —$(CR_2)_n$—Ar—$(CR_2)_p$—*, —$(CR_2)_p$—Ar—$(CR_2)_n$—*, —$O(CR_2)_n$—Ar—$(CR_2)_p$—*, and —$(CR_2)_p$—Ar—$(CR_2)_nO$—*, wherein  indicates the position of a covalent bond with the moiety:

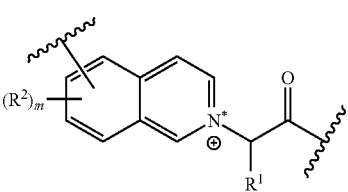

and
*** indicates the position of a covalent bond with $R^3$; each instance of n is independently a whole number selected from 1-20; each instance of p is independently an integer selected from 0-20; and R for each instance is independently selected from hydrogen, alkyl, cycloalkyl, and aryl; or two instances of R taken together with the carbons to which they are attached form a 3-6 membered carbocyclic ring; or two instances of R taken together with the atoms to which they are attached form a 5-6 membered heterocyclic ring.

In a seventh embodiment of the first aspect, provided herein is the polypeptide conjugate of the sixth embodiment of the first aspect, wherein the linker is absent or selected from the group consisting of —$(CR_2)_n$—*, —O (CR$_2$)$_n$—*, —(OCR$_2$CR$_2$)$_n$—*, —(OCR$_2$CR$_2$)$_n$OAr—*, and —(OCR$_2$CR$_2$)$_n$Ar—*, wherein R is hydrogen and n is a whole number selected from 1-6.

In an eighth embodiment of the first aspect, provided herein is the polypeptide conjugate of the seventh embodiment of the first aspect, wherein the polypeptide is hemoglobin.

In a ninth embodiment of the first aspect, provided herein is the polypeptide conjugate of the eighth embodiment of the first aspect, wherein R$^3$ is selected from the group consisting of:

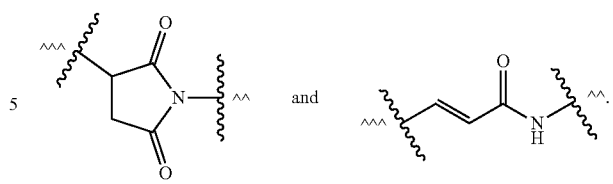

In a tenth embodiment of the first aspect, provided herein is the polypeptide conjugate of the first aspect, wherein the polypeptide conjugate is selected from the group consisting of:

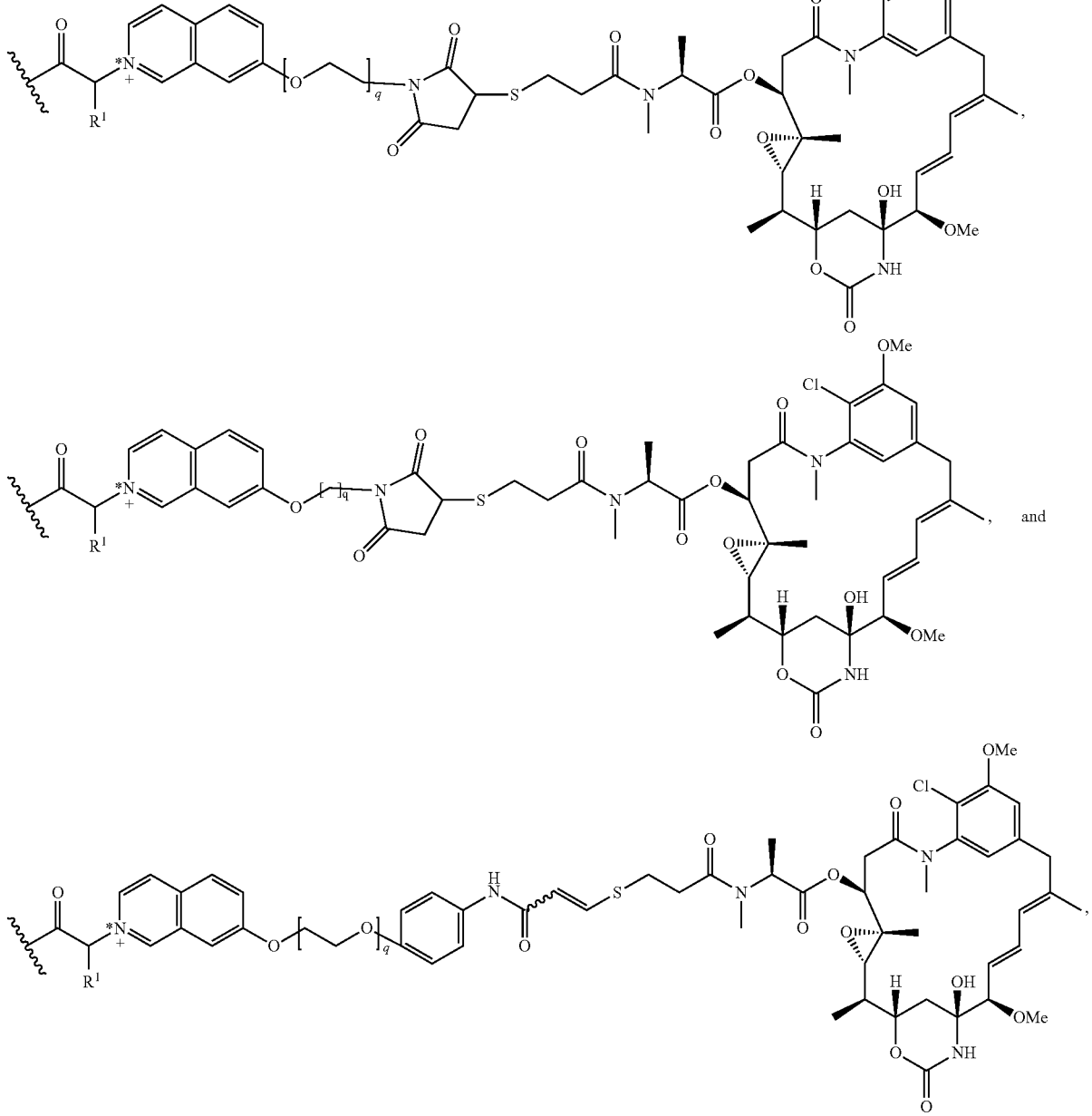

wherein q is a whole number selected from 1-10.

In an eleventh embodiment of the first aspect, provided herein is the polypeptide conjugate of the first aspect, wherein the polypeptide conjugate is selected from the group consisting of:

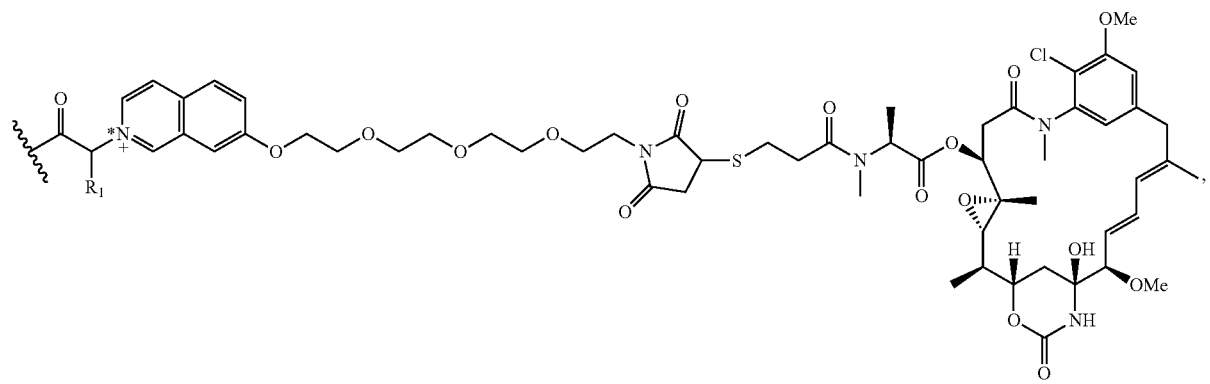

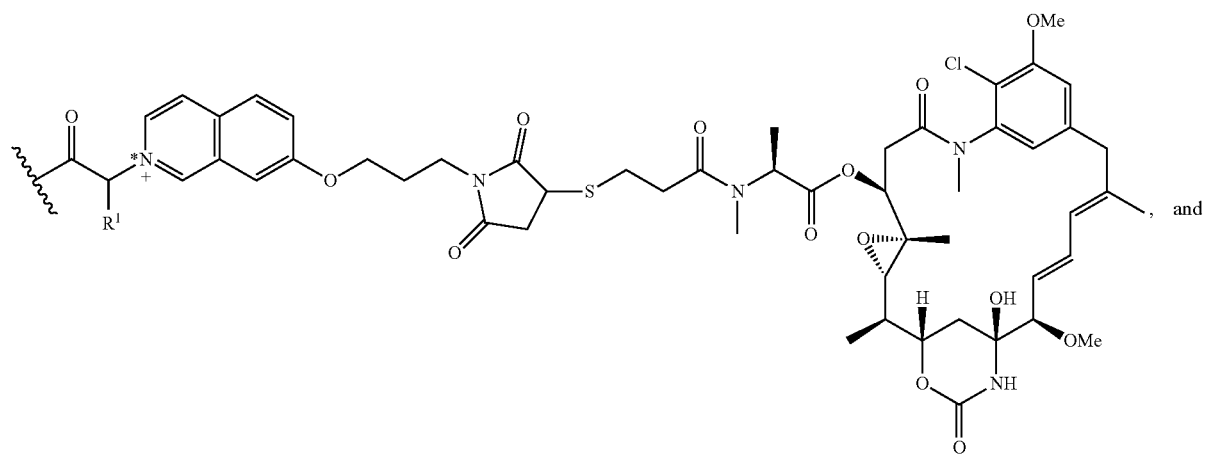

, and

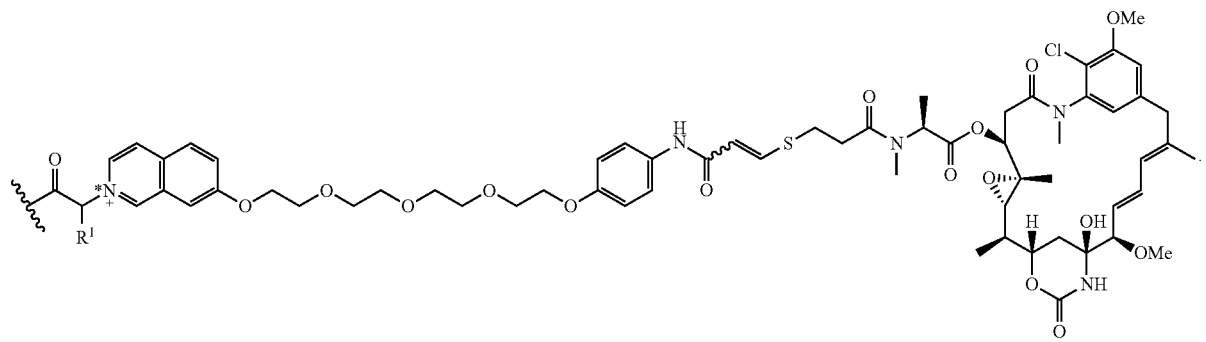

In a twelfth embodiment of the first aspect, provided herein is the polypeptide conjugate of the first aspect, wherein the polypeptide comprises one or more lysine amino acids comprising a side chain represented by the structure of Formula 2:

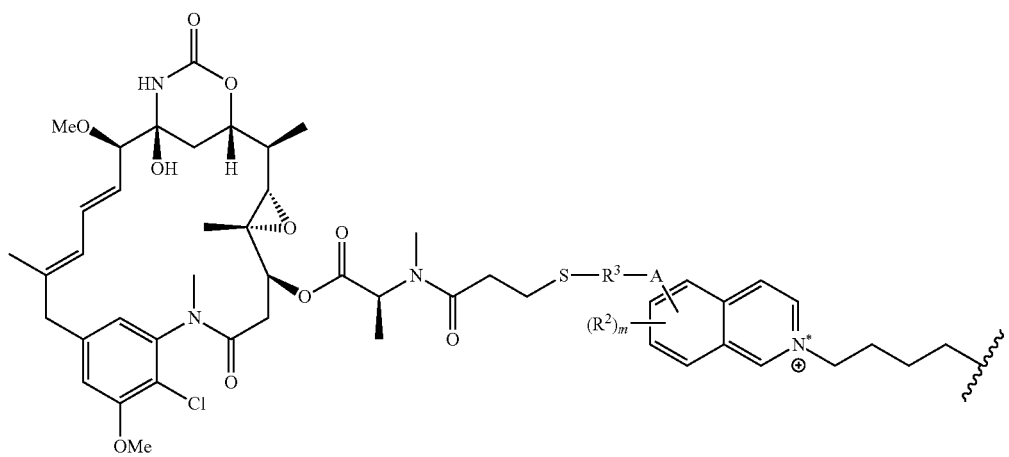

20 wherein N** represents the lysine side chain nitrogen.

In a second aspect, provided is a method of preparing the polypeptide conjugate of the first aspect comprising the step of contacting a compound of Formula 3:

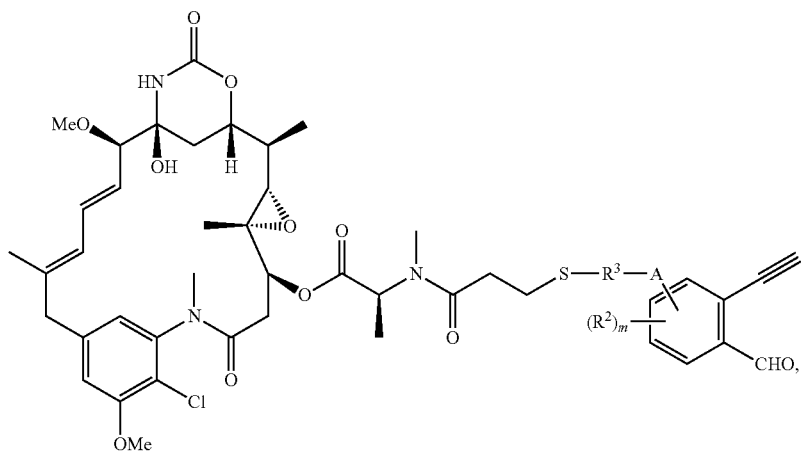

wherein $R^2$ independently for each instance is selected from the group consisting of hydrogen, alkyl, alkenyl, alkynyl, cycloalkyl, aryl, aralkyl, heterocycloalkyl, heteraryl, halide, cyano, nitro, hydroxyl, —$OR^4$, —$SR^4$, —(C=O)$OR^4$, —O(C=O)$R^4$, —N($R^4$)$_2$, —(C=O)N($R^4$)$_2$, —N($R^4$)(C=O)$R^4$, —N($R^4$)(C=O)N($R^4$)$_2$, —SO$_2R^4$, —N($R^4$)SO$_2R^4$, and —SO$_2$N($R^4$)$_2$;

$R^3$ is selected from the group consisting of:

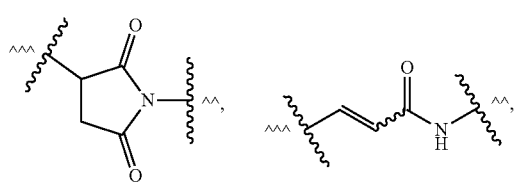

-continued

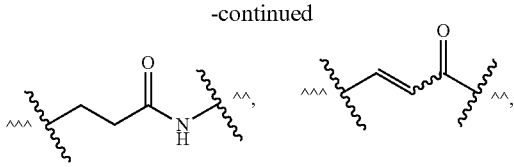

and

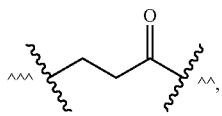 [SMILES: *CCC(*)=O]

wherein ⁀⁀ indicates the position of a covalent bond with A and ⁀⁀⁀ indicates the position of a covalent bond with the moiety:

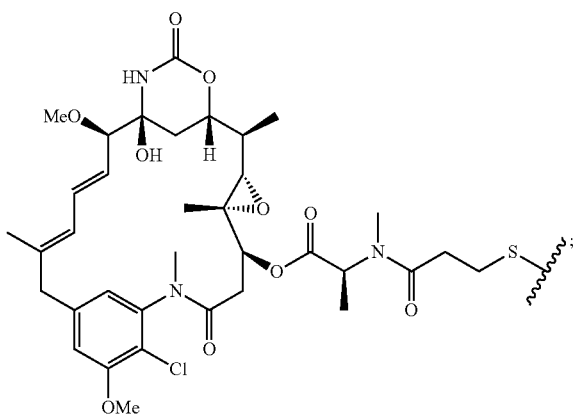

with a polypeptide comprising an N-terminal amino acid represented by the structure shown below:

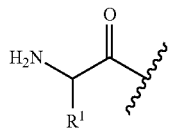

or a conjugate salt or zwitterion thereof, wherein $R^1$ is the side chain of the N-terminal amino acid of the polypeptide and the N-terminal amino acid is a natural amino acid or a non-natural amino acid; thereby forming the polypeptide conjugate of claim 1.

In a first embodiment of the second aspect, provided herein is the method of the second aspect, wherein $R^3$ is

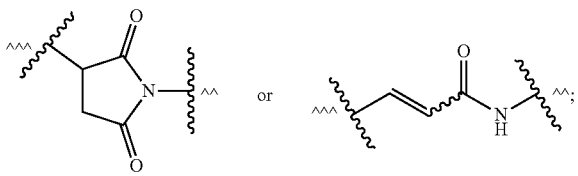 [SMILES: *C1CC(=O)N(*)C1=O ; *C=CC(=O)N*]

and the linker is absent or selected from the group consisting of —$(CR_2)_n$—*, —$O(CR_2)_n$—*, —$(OCR_2CR_2)_n$—*, —$(OCR_2CR_2)_nOAr$—*, and —$(OCR_2CR_2)_nAr$—*, wherein R is hydrogen and n is a whole number selected from 1-6.

In a second embodiment of the second aspect, provided herein is the method of the second aspect, wherein the polypeptide is hemoglobin.

In a third aspect, provided herein is a pharmaceutical composition comprising the polypeptide conjugate of the first aspect and at least one pharmaceutically acceptable excipient.

In a fourth aspect, provided herein is a method of treating cancer in a subject in need thereof comprising the step of administering a pharmaceutically effective amount of the polypeptide conjugate of the first aspect to the subject.

In a first embodiment of the fourth aspect, provided herein is the method of the second aspect, wherein the cancer is selected from the group consisting of pancreatic cancer, leukemia, head and neck cancer, colorectal cancer, lung cancer, breast cancer, liver cancer, nasopharyngeal cancer, esophageal cancer brain cancer, acute lymphocytic leukemia, ovarian cancer, thymoma, melanoma, and non-small scale lung cancer.

In a second embodiment of the fourth aspect, provided herein is the method of the second aspect, wherein the cancer is wherein said cancer is hepatocellular carcinoma, liver cancer progenitor cells-induced tumor, glioblastoma, or triple negative progenitor cell induced tumor.

BRIEF DESCRIPTION OF THE DRAWINGS

The above and other objects and features of the present disclosure will become apparent from the following description of the disclosure, when taken in conjunction with the accompanying drawings.

FIG. 2 depicts (A) exemplary mertansine conjugation reagent for use in a one-step N-terminal selective conjugation reaction; and (B) an exemplary conjugation reagent for use in a two-step N-terminal selective conjugation reaction.

FIG. 3E depicts liquid chromatography-mass spectrometry (LC-MS) results for an exemplary hemoglobin N-terminal N-acetyl cysteine conjugate.

FIG. 7 shows the polypeptide sequences for hemoglobin di-alpha chain (SEQ ID NO: 1 and 4) and beta chain (SEQ ID NO: 2, 3, and 5) according to certain embodiments described herein.

DETAILED DESCRIPTION

Definitions

Figure 1:
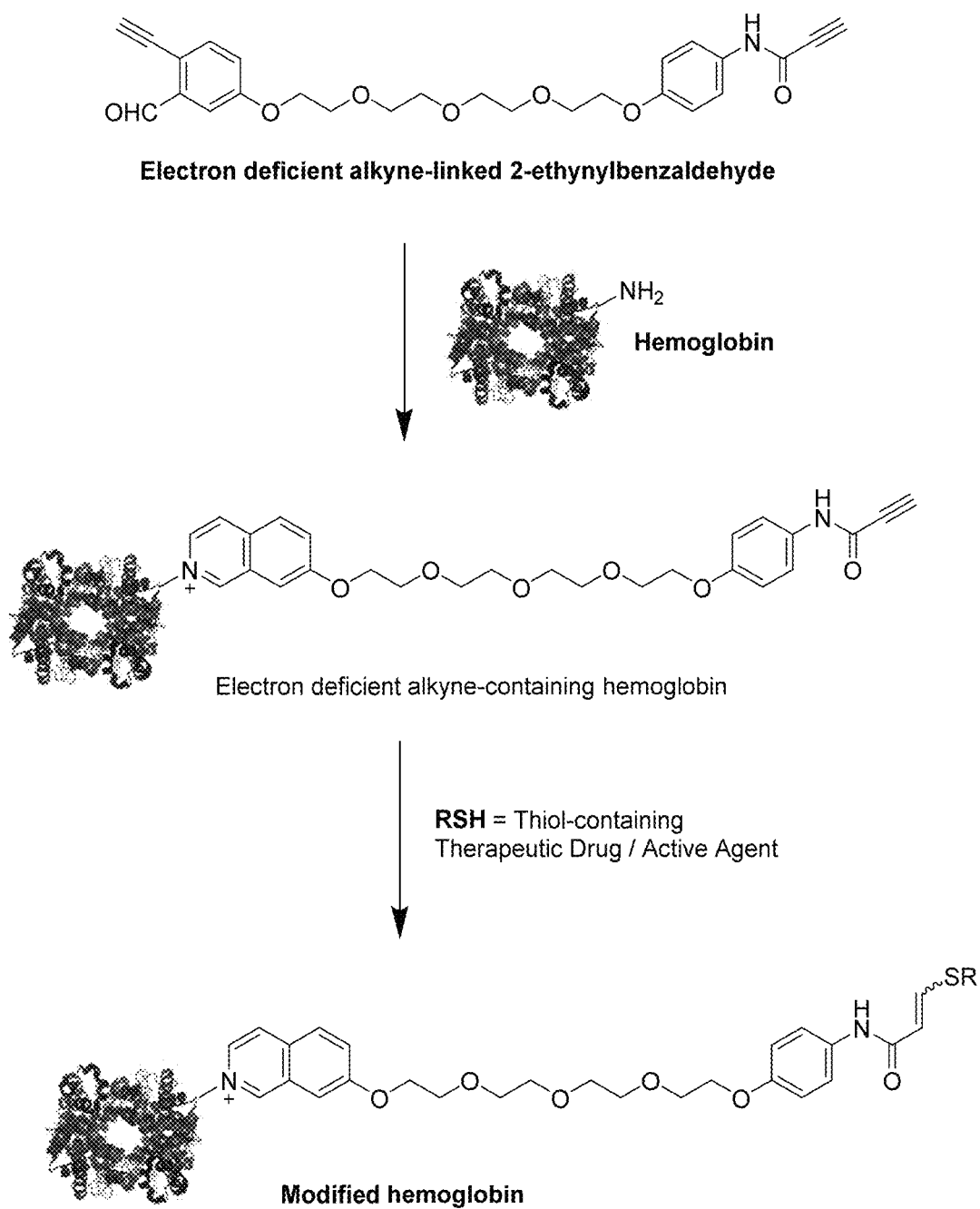
FIG. 1 depicts an exemplary two-step synthetic sequence for N-terminal selective functionalization of hemoglobin according to certain embodiments described herein.
Figure 3A:
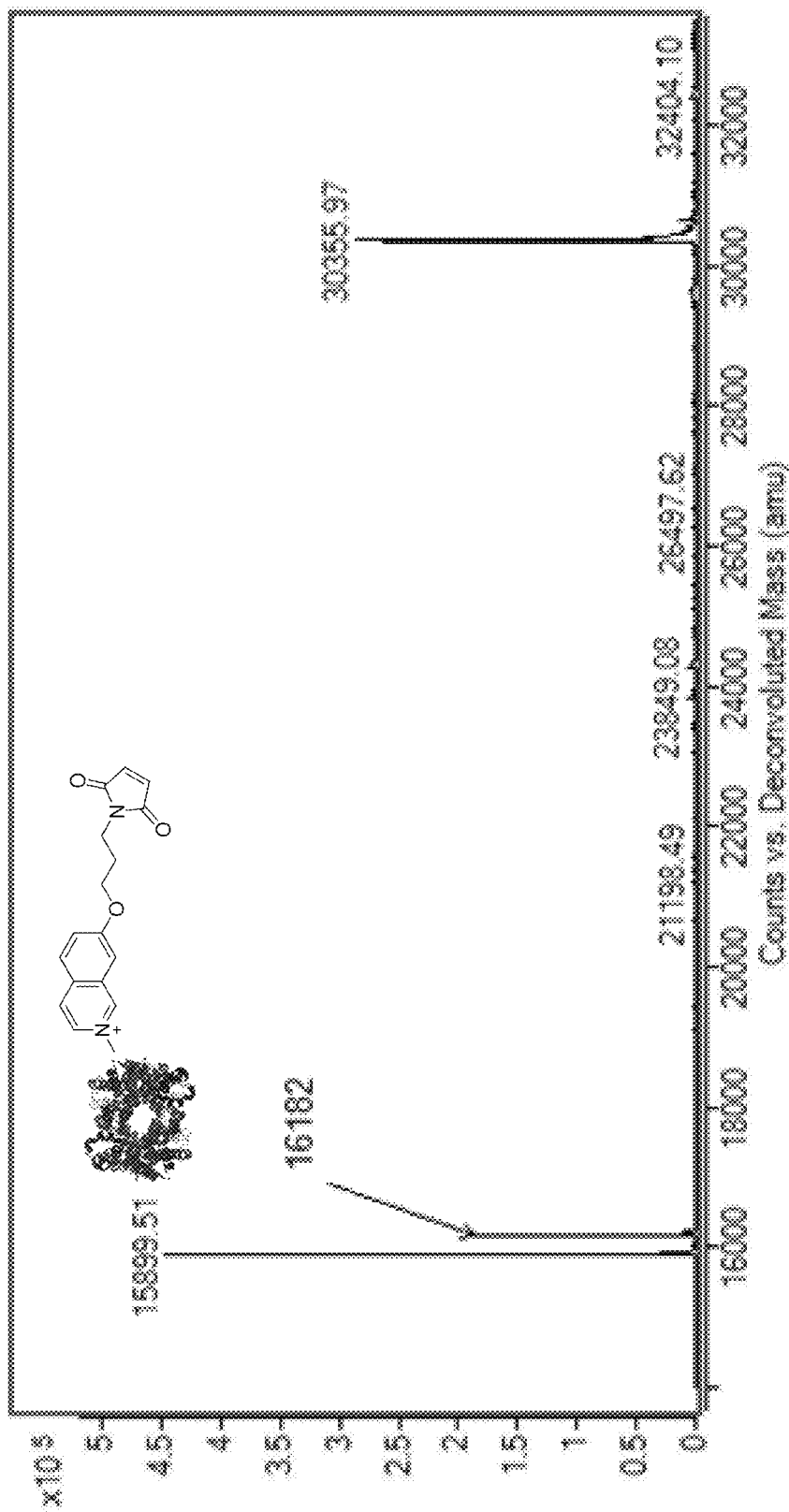
FIG. 3A depicts liquid chromatography-mass spectrometry (LC-MS) results of an exemplary hemoglobin conjugate comprising a maleimide group.
Figure 3B:
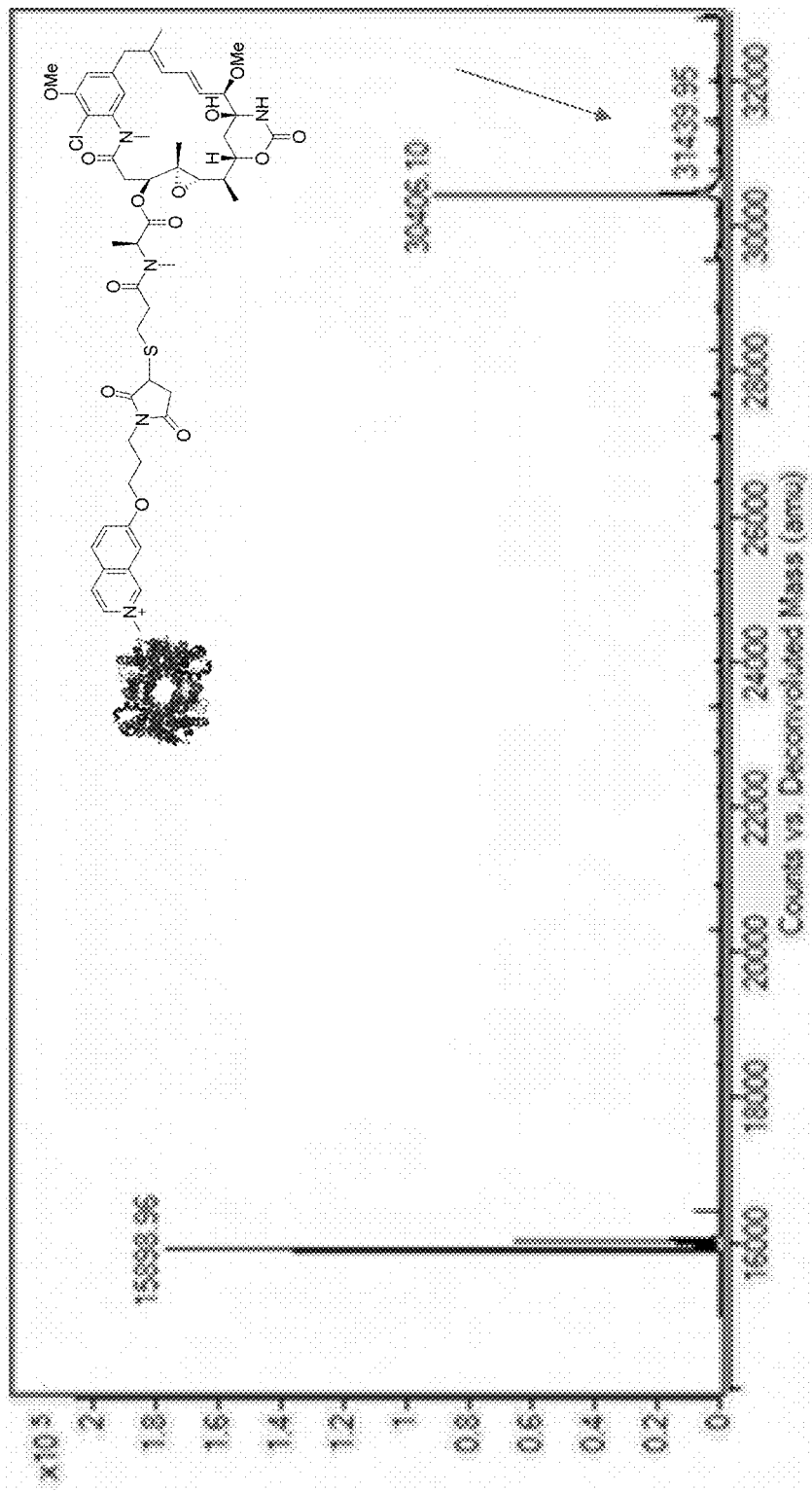
FIG. 3B depicts liquid chromatography-mass spectrometry (LC-MS) results of an exemplary hemoglobin mertansine conjugate according to certain embodiments described herein.
Figure 3C:
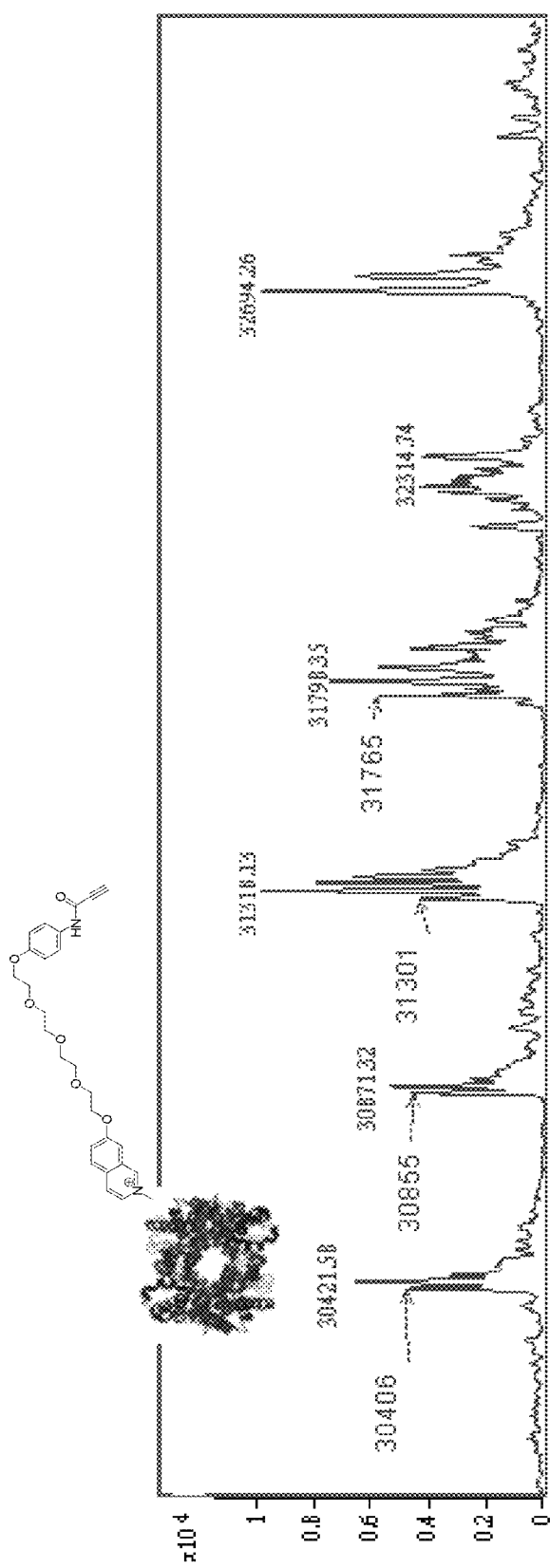
FIG. 3C depicts liquid chromatography-mass spectrometry (LC-MS) results of an exemplary hemoglobin N-terminal conjugate comprising a reactive alkyne.
Figure 3D:
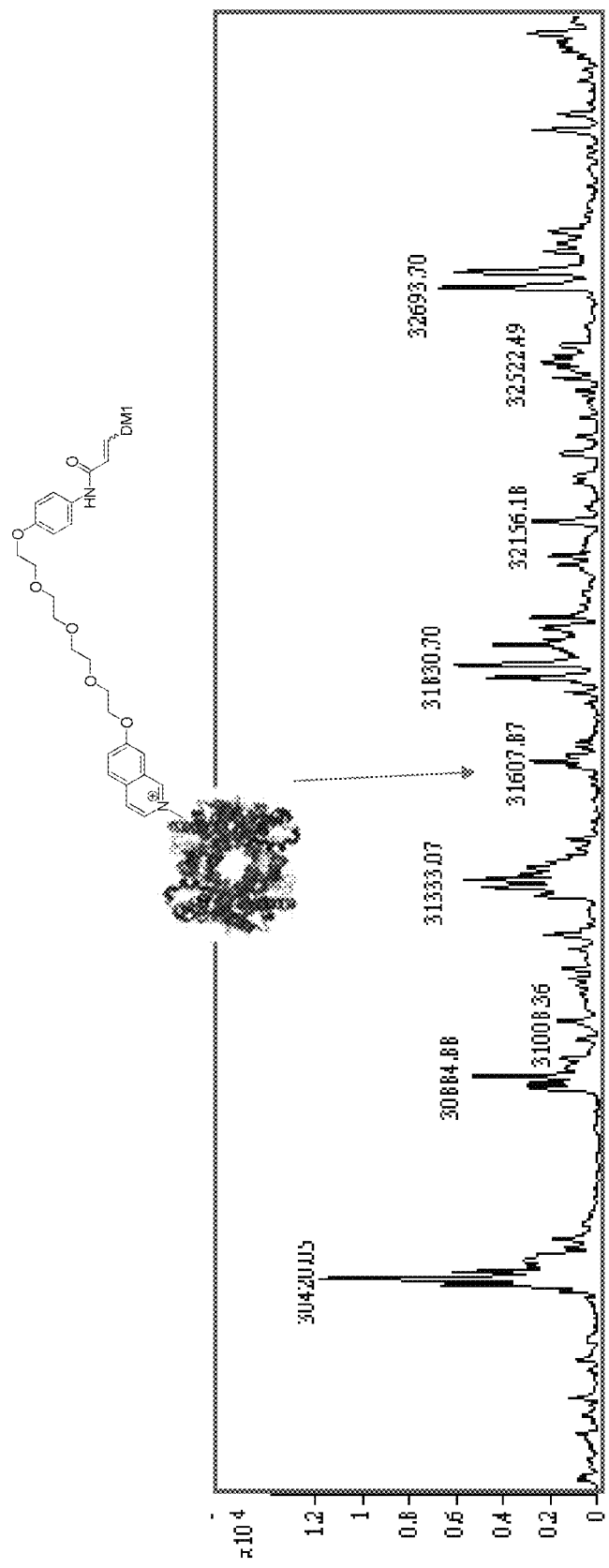
FIG. 3D depicts liquid chromatography-mass spectrometry (LC-MS) results of an exemplary hemoglobin N-terminal mertansine conjugate according to certain embodiments described herein.
Figure 3F:
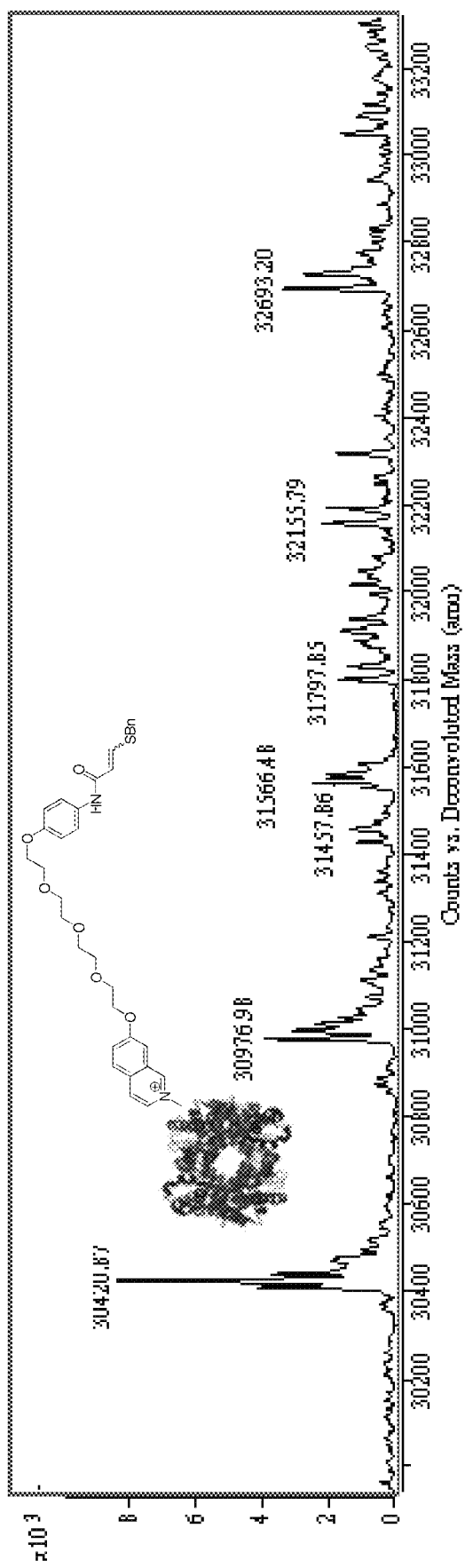
FIG. 3F depicts liquid chromatography-mass spectrometry (LC-MS) results for an exemplary hemoglobin benzyl mercaptan conjugate.
Figure 4A:
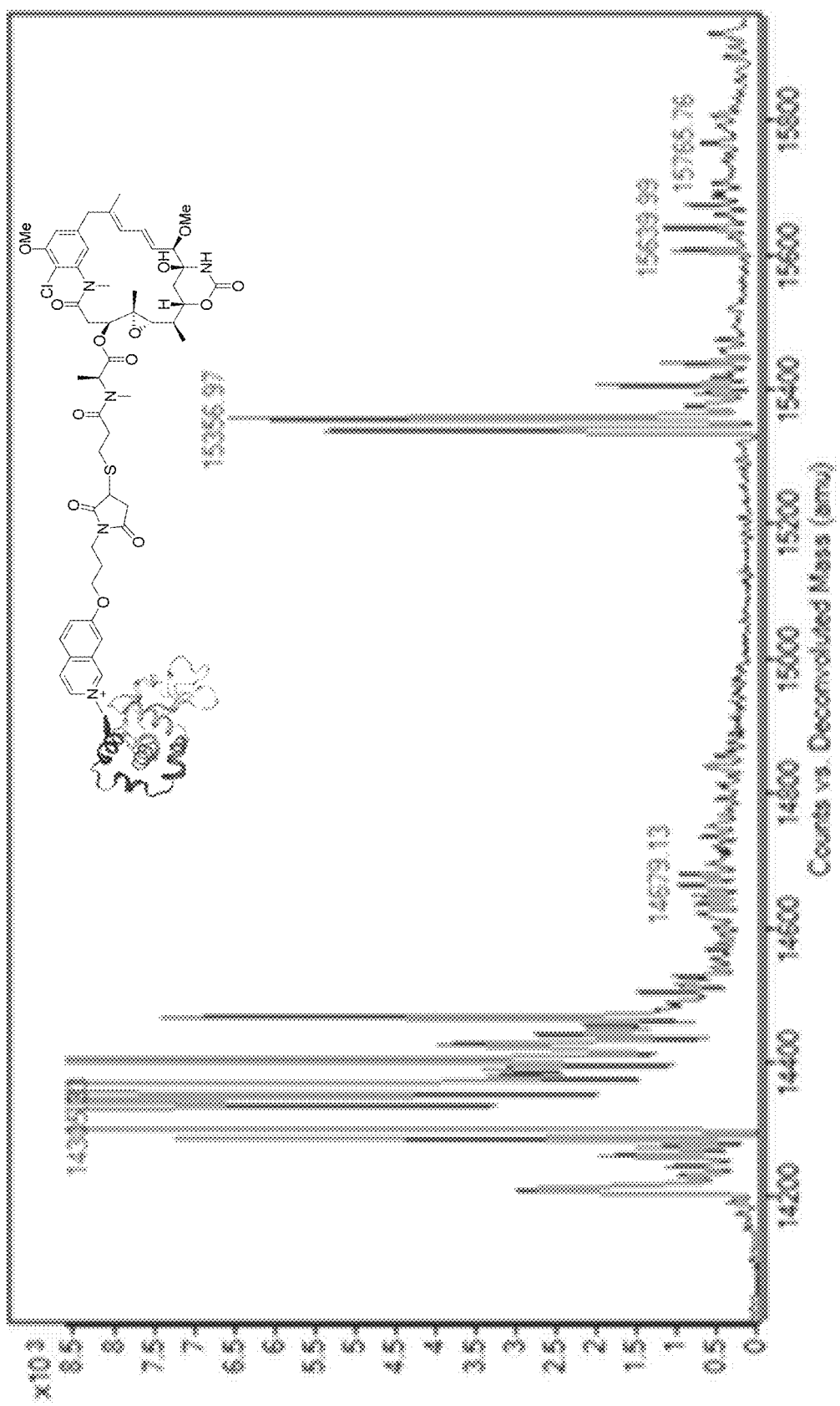
FIG. 4A depicts liquid chromatography-mass spectrometry (LC-MS) results for an exemplary RNase mertansine conjugate according to certain embodiments described herein.
Figure 4B:
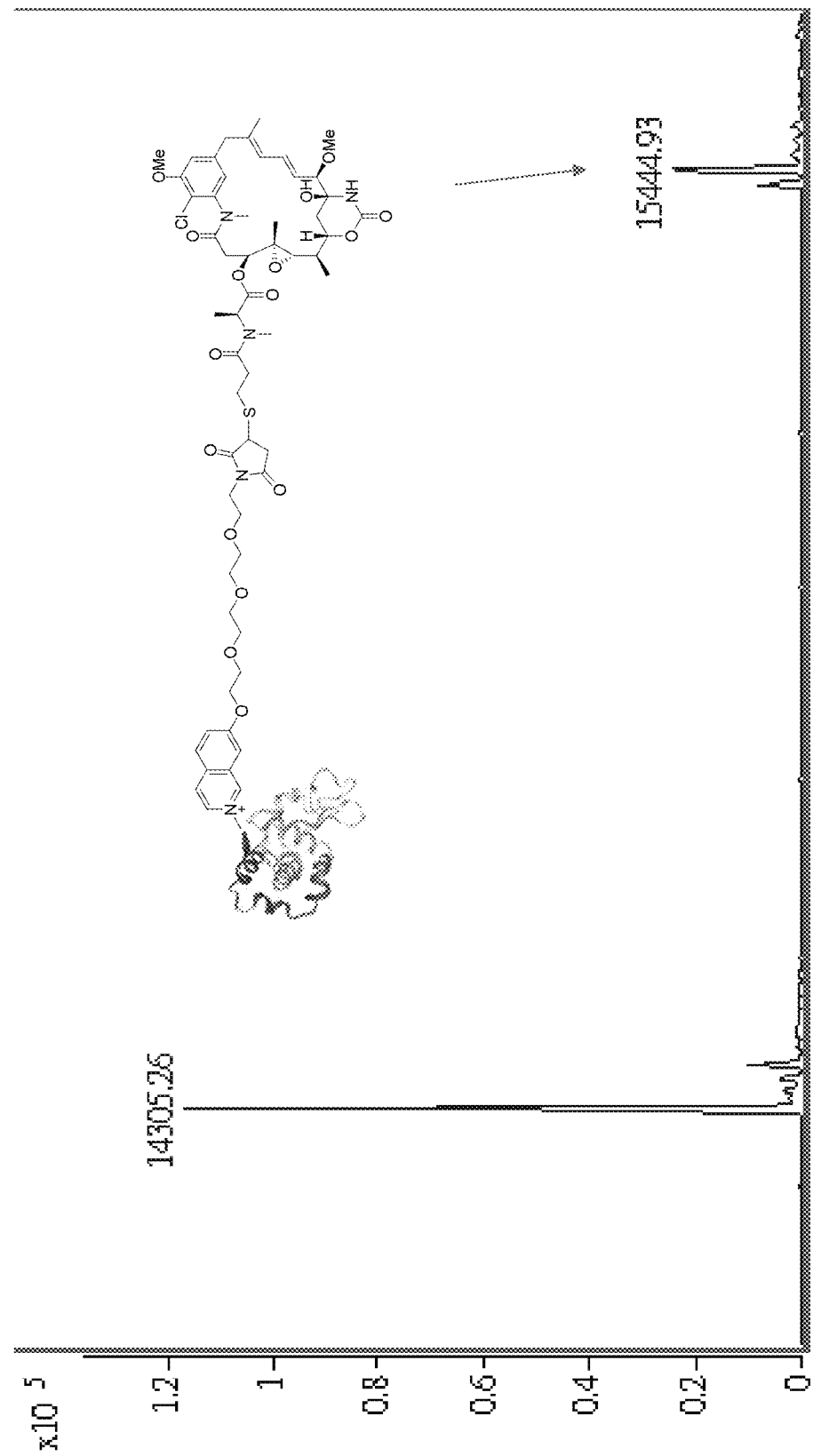
FIG. 4B depicts liquid chromatography-mass spectrometry (LC-MS) results for an exemplary RNase mertansine conjugate according to certain embodiments described herein.
Figure 4C:
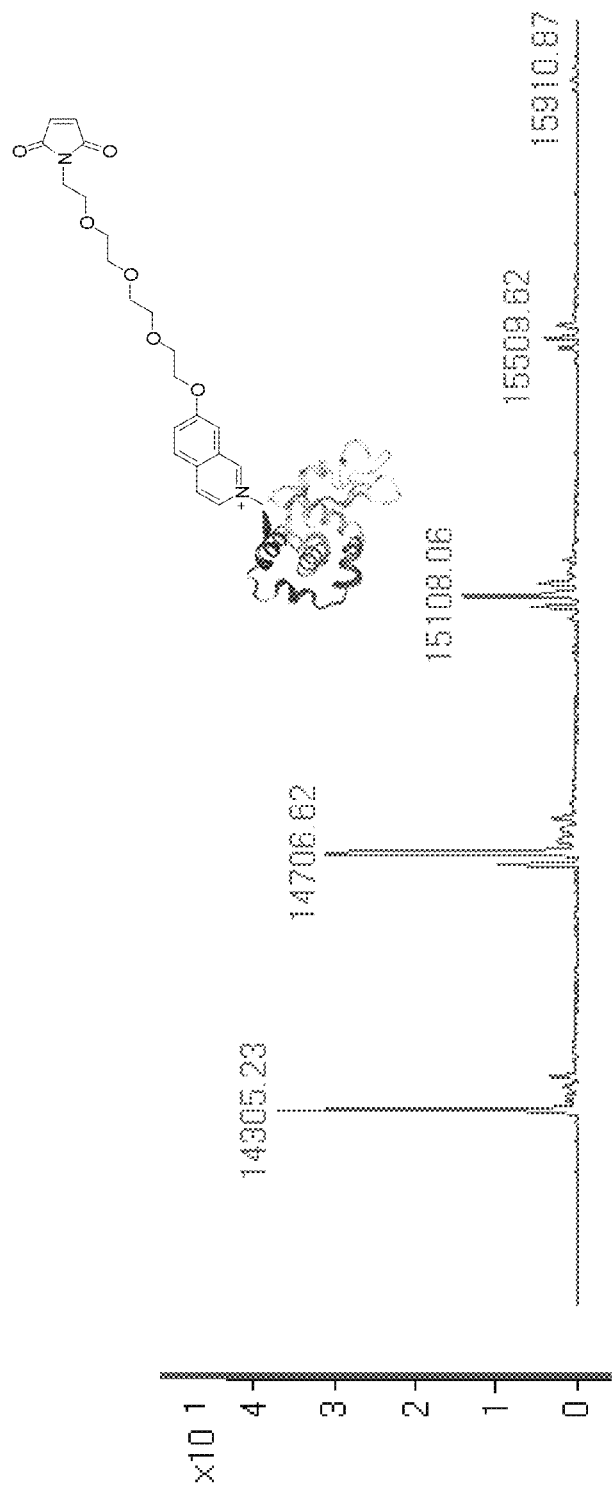
FIG. 4C depicts liquid chromatography-mass spectrometry (LC-MS) results for an exemplary RNase conjugate comprising a maleimide.
Figure 4D:
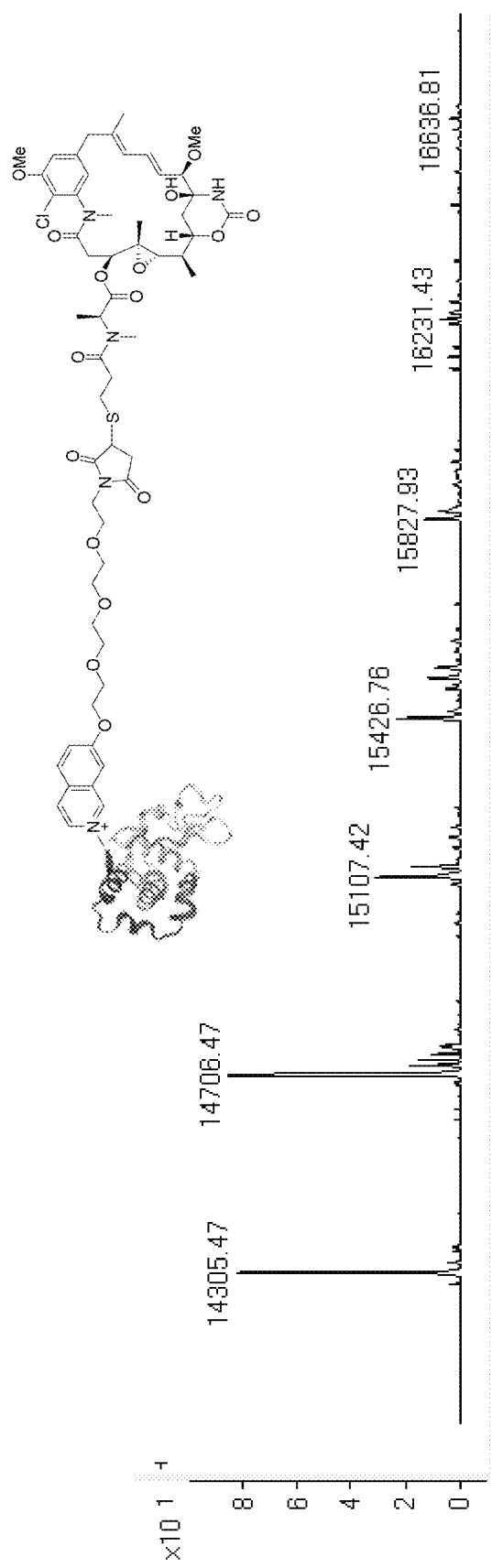
FIG. 4D depicts liquid chromatography-mass spectrometry (LC-MS) results for an exemplary RNase mertansine conjugate according to certain embodiments described herein.
Figure 5A:
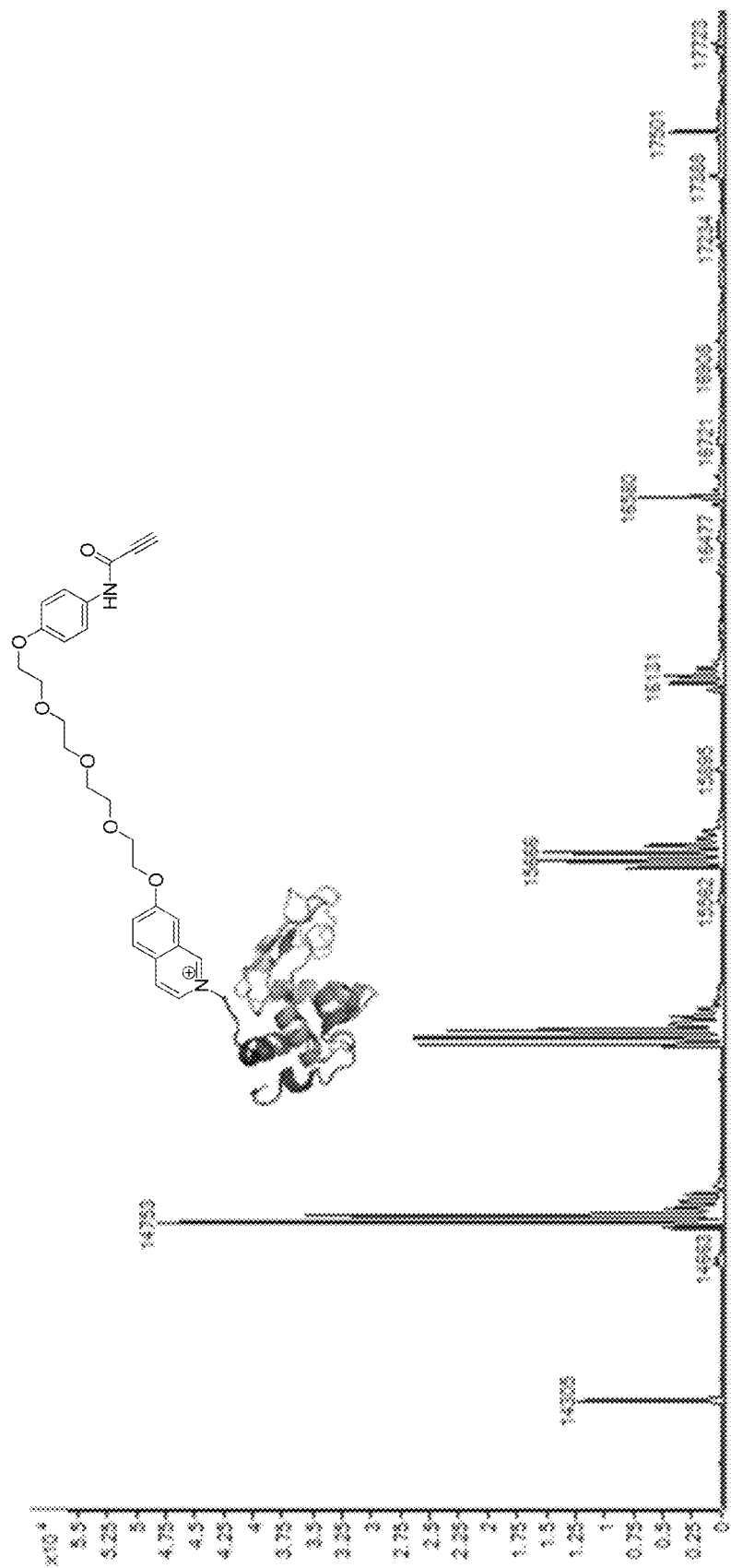
FIG. 5A depicts liquid chromatography-mass spectrometry (LC-MS) results for an exemplary lysozyme N-terminal conjugated with 2-ethynylbenzaldehyde $(OCH_2CH_2)_4$ linked electron deficient alkyne.
Figure 5B:
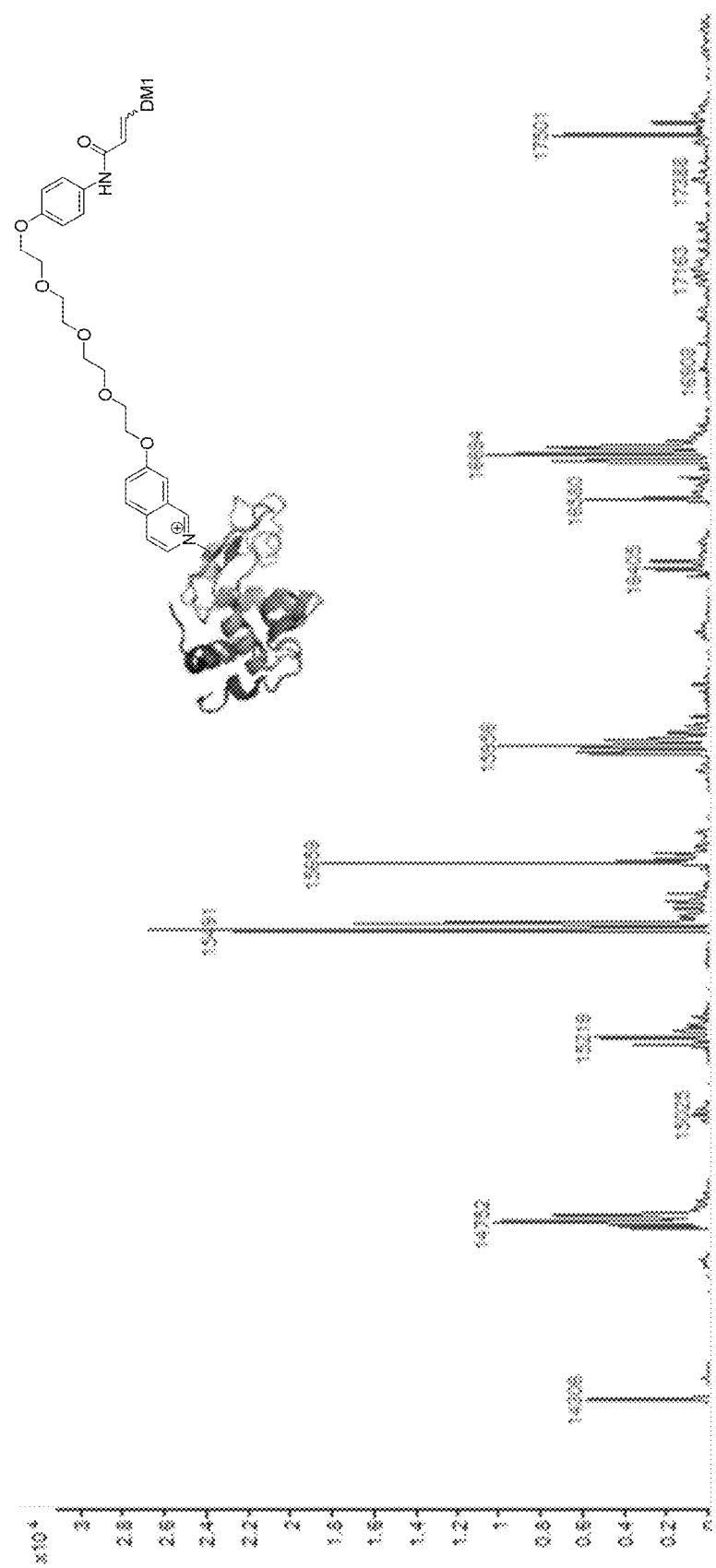
FIG. 5B depicts liquid chromatography-mass spectrometry (LC-MS) results for the coupling reaction of 2-ethynylbenzaldehyde $(OCH_2CH_2)_4$ linked electron deficient alkyne and mertansine according to certain embodiments described herein.
Figure 6A:
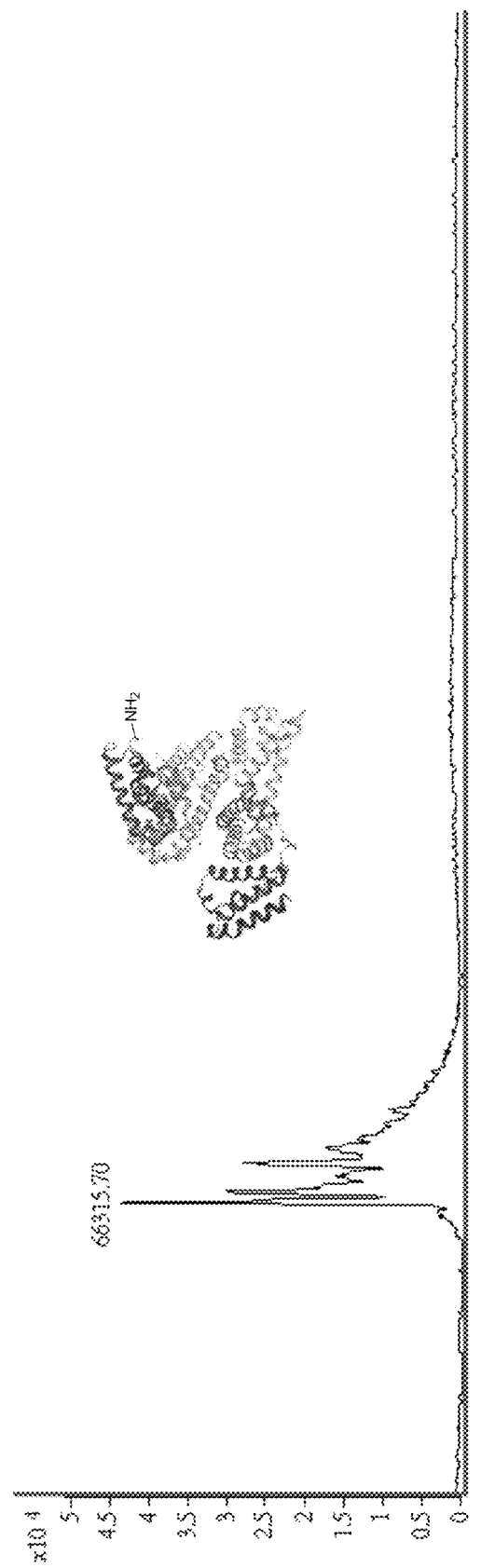
FIG. 6A depicts LC-MS results of bovine serum albumin with the N-terminal amine depicted.
Figure 6B:
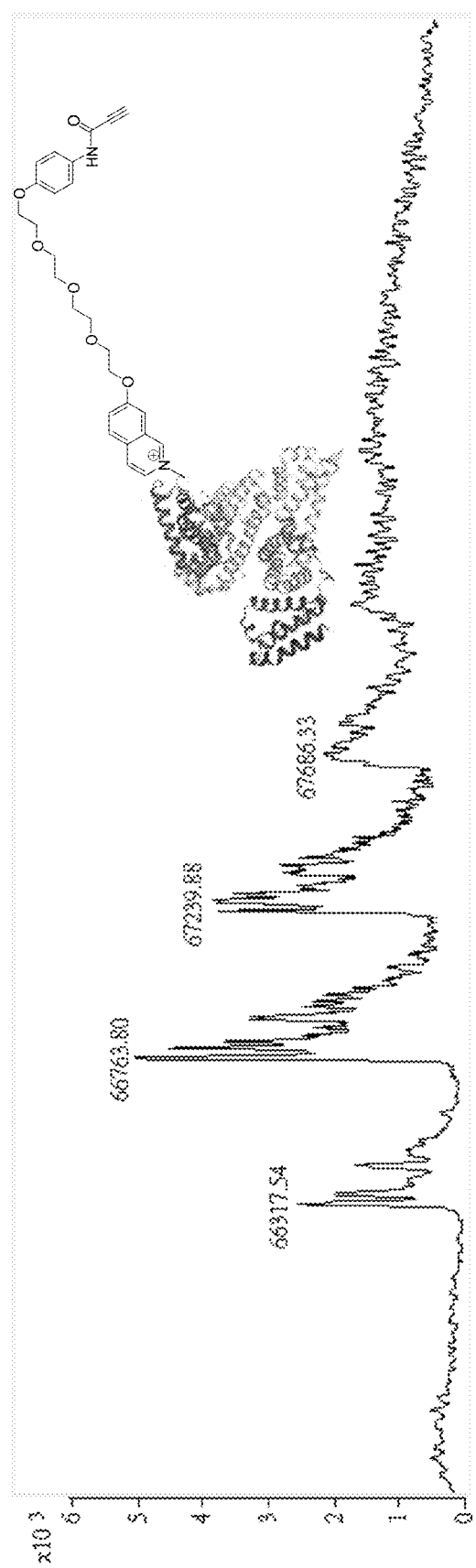
FIG. 6B depicts LC-MS results of bovine serum albumin N-terminal functionalized with 2-ethynylbenzaldehyde $(OCH_2CH_2)_4$ linked electron deficient alkyne.
Figure 6C:
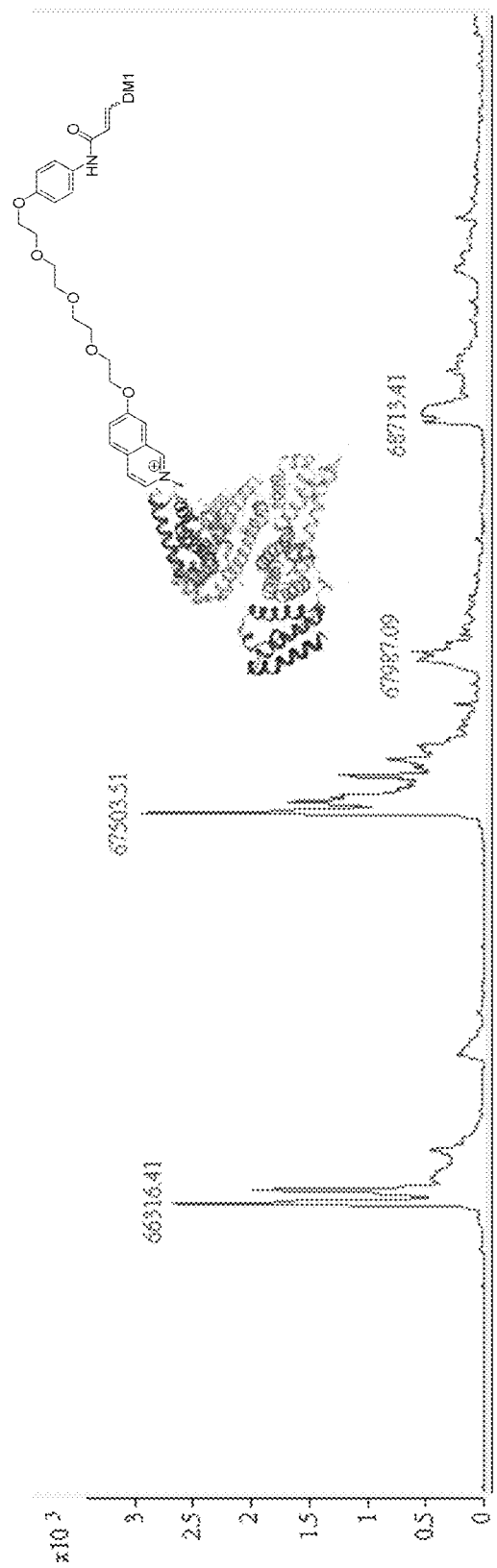
FIG. 6C depicts the LC-MS of the product of coupling reaction of 2-ethynylbenzaldehyde $(OCH_2CH_2)_4$ linked electron deficient alkyne and mertansine according to certain embodiments described herein.

The definitions of terms used herein are meant to incorporate the present state-of-the-art definitions recognized for each term in the field of biotechnology. Where appropriate, exemplification is provided. The definitions apply to the terms as they are used throughout this specification, unless otherwise limited in specific instances, either individually or as part of a larger group.

When trade names are used herein, applicants intend to independently include the trade name product formulation, the generic drug, and the active pharmaceutical ingredient(s) of the trade name product.

The term "antibody" as used herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. In certain embodiments, antibodies are polyclonal, monoclonal, bispecific, human, humanized or chimeric antibodies, single chain antibodies, Fv, Fab fragments, F(ab') fragments, F(ab')$_2$ fragments, anti-idiotypic (anti-Id) antibodies, CDR's, and epitope-binding fragments of any of the above which immunospecifically bind to an antigen, such as cancer cell antigens, viral antigens, or microbial antigens.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

A "non-natural amino acid" refers to an amino acid that is not one of the 20 common amino acids or pyrrolysine or selenocysteine; other terms that may be used synonymously with the term "non-natural amino acid" is "non-naturally encoded amino acid," "unnatural amino acid," "non-naturally-occurring amino acid," and the like. The term "non-natural amino acid" includes, but is not limited to, amino acids that have the same basic chemical structure as a naturally occurring amino acid, i.e., an a carbon that is bound to a hydrogen, a carboxyl group, an amino group, and an R group, as well as amino acids that amino acids in which the amino group is attached at the β or γ carbon.

The term "hemoglobin" refers generally to the protein contained within red blood cells that transports oxygen. Each molecule of hemoglobin has 4 subunits, 2 α chains and 2 β chains, which are arranged in a tetrameric structure. Each subunit also contains one heme group, which is the iron-containing center that binds oxygen. Thus, each hemoglobin molecule can bind 4 oxygen molecules.

The term "modified hemoglobin" includes, but is not limited to, hemoglobin altered by a chemical reaction such as intra- and inter-molecular cross-linking, genetic manipulation and polymerization. As used herein, the term "hemoglobin" by itself refers both to native, unmodified, hemoglobin, as well as modified hemoglobin.

The term "protein", "polypeptide", or "peptide" as used herein indicates an organic polymer composed of two or more amino acid monomers and/or analogs thereof. The term "polypeptide" or "peptide" includes amino acid polymers of any length including full length proteins and peptides, as well as analogs and fragments thereof. A polypeptide of three or more amino acids is also called an oligopeptide. As used herein, the term "amino acid", "amino acidic monomer", or "amino acid residue" refers to any of the twenty naturally occurring amino acids.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" and "sulfone" is art-recognized and refers to —SO$_2$—. "Halide" designates the corresponding anion of the halogens.

Provided herein is a polypeptide conjugate represented by the structure of Formula 1:

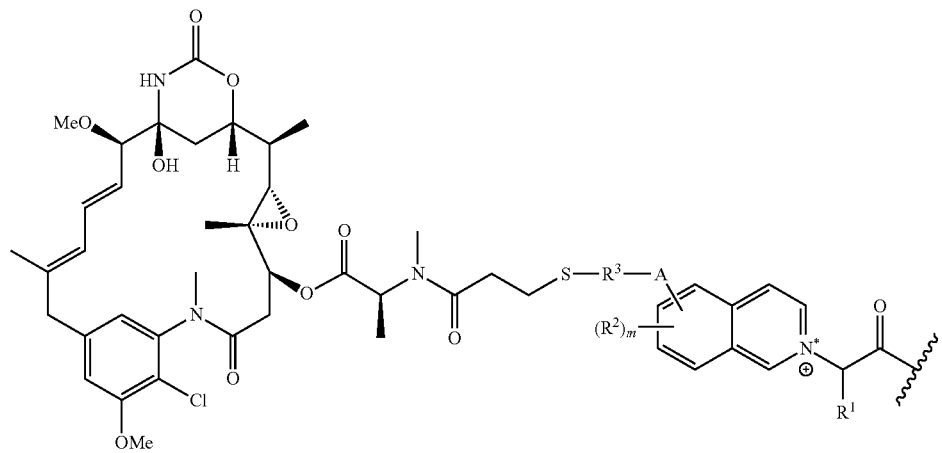

or a conjugate salt or zwitterion thereof, wherein

A is a linker or is absent;

m is a whole number selected from 1-3;

N* is the N-terminal nitrogen of the polypeptide conjugate;

R$^1$ is the side chain of the N-terminal amino acid of the polypeptide conjugate;

R$^2$ independently for each instance is selected from the group consisting of hydrogen, alkyl, alkenyl, alkynyl, cycloalkyl, aryl, aralkyl, heterocycloalkyl, heteroaryl, halide, cyano, nitro, hydroxyl, —OR$^4$, —SR$^4$, —(C=O)OR$^4$, —O(C=O)R$^4$, —N(R$^4$)$_2$, —(C=O)N(R$^4$)$_2$, —N(R$^4$)(C=O)R$^4$, —N(R$^4$)(C=O)N(R$^4$)$_2$, —SO$_2$R$^4$, —N(R$^4$)SO$_2$R$^4$, and —SO$_2$N(R$^4$)$_2$;

R$^3$ is selected from the group consisting of:

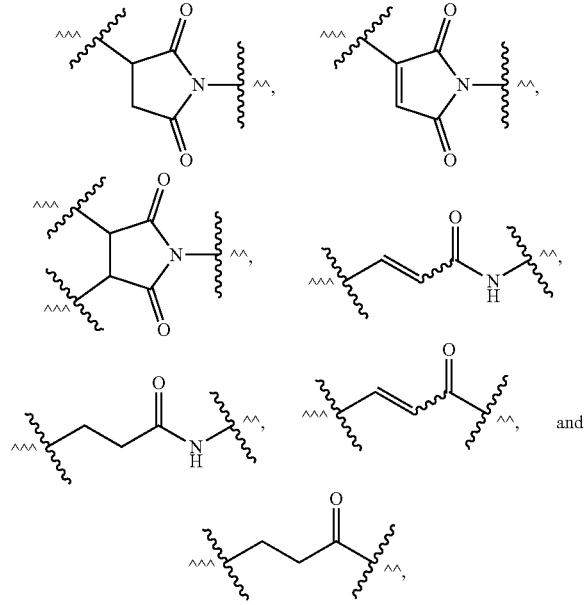

wherein ^^ indicates the position of a covalent bond with A and ^^^ indicates the position of a covalent bond with the moiety:

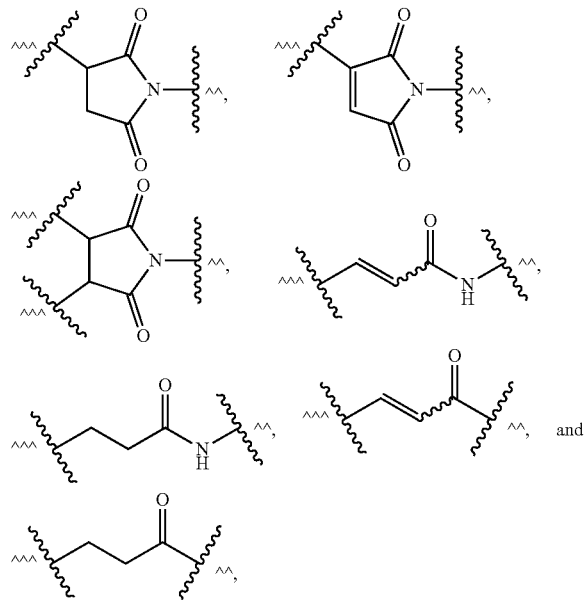

and

R$^4$ for each instance is independently selected from the group consisting of hydrogen, alkyl, alkenyl, alkynyl, cycloalkyl, aryl, aralkyl, heterocycloalkyl, and heteraryl; or two instances of R$^4$ taken together with the atoms to which they are attached form a 5-6 membered heterocycloalkyl.

The polypeptide conjugate of Formula 1 comprises a cation and can thus exist as a pharmaceutically acceptable salt comprising the polypeptide conjugate of Formula 1 and a pharmaceutically acceptable anion. The pharmaceutically acceptable salt may comprise any counterion that has been previously used in a FDA-approved drug and/or are generally recognized as safe (GRAS). In certain embodiments, the pharmaceutically anion is selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, and tosylate, and the like.

In alternative embodiments, the polypeptide conjugate of Formula 1 exists as a zwitterion. In such embodiments, the cation in polypeptide conjugate of Formula 1 is balanced by an anion present in the polypeptide conjugate of Formula 1, e.g., in the polypeptide, such as in an amino acid side chain comprising an anion (e.g., a carboxylate) or the C-terminal carboxylate of the polypeptide.

In certain embodiments of the polypeptide conjugate of Formula 1, the linker is absent or selected from the group consisting of —(CR$_2$)$_n$—*, —O(CR$_2$)$_n$—*, —(CR$_2$)$_n$O—*, —O(CR$_2$)$_n$O—*, —(CR$_2$)$_n$C(=O)—*, —C(=O)(CR$_2$)$_n$—*, —C(=O)O(CR$_2$)$_n$—*, —(CR$_2$)$_n$OC(=O)—*, —O(CR$_2$)$_n$C(=O)—*, —O(CR$_2$)$_n$C(=O)N(R)(CR$_2$)$_p$—*, —O(CR$_2$)$_n$N(R)C(=O)N(R)(CR$_2$)$_p$—*, —O(CR$_2$)$_n$C(=O)O(CR$_2$)$_p$—*, —O(CR$_2$)$_n$OC(=O)N(R)(CR$_2$)$_p$—*, —C(=O)(CR$_2$)$_n$O—, —O(CR$_2$)$_n$N(R)C(=O)—*, —O(CR$_2$)$_n$N(R)C(=O)(CR$_2$)$_p$—*, —C(=O)N(R)(CR$_2$)$_n$O—*, —OC(=O)(CR$_2$)$_n$—*, —(CR$_2$)$_n$C(=O)O—*, —OC(=O)O(CR$_2$)$_n$—*, —(CR$_2$)$_n$OC(=O)O—*, —C(=O)N(R)(CR$_2$)$_n$—*, —(CR$_2$)$_n$(R)NC(=O)—, —N(R)C(=O)(CR$_2$)$_n$—*, —(CR$_2$)$_n$C(=O)N(R)—*, —N(R)C(=O)O(CR$_2$)$_n$—*, —(CR$_2$)$_n$OC(=O)N(R)—, —OC(=O)N(R)(CR$_2$)$_n$—*, —(CR$_2$)$_n$N(R)C(=O)O—*, —(OCR$_2$CR$_2$)$_n$—*, —(CR$_2$CR$_2$O)$_n$—*, —(OCR$_2$CR$_2$)$_n$OAr—*, —(OCR$_2$CR$_2$)$_n$Ar—*, —(OCR$_2$CR$_2$)$_n$(C=O)—*, —(OCR$_2$CR$_2$)$_n$O(C=O)—*, —(OCR$_2$CR$_2$)$_n$N(R)(C=O)—*, —(OCR$_2$CR$_2$)$_n$(C=O)(CR$_2$)$_p$—*, —(OCR$_2$CR$_2$)$_n$O(C=O)(CR$_2$)$_p$—*, —(OCR$_2$CR$_2$)$_n$N(R)(C=O)(CR$_2$)$_p$—*, —(OCR$_2$CR$_2$)$_n$(C=O)O(CR$_2$)$_p$—*, —(OCR$_2$CR$_2$)$_n$O(C=O)O(CR$_2$)$_p$—*, —(OCR$_2$CR$_2$)$_n$N(R)(C=O)O(CR$_2$)$_p$—*, —(OCR$_2$CR$_2$)$_n$(C=O)N(R)(CR$_2$)$_p$—*, —(OCR$_2$CR$_2$)$_n$O(C=O)N(R)(CR$_2$)$_p$—*, —(OCR$_2$CR$_2$)$_n$N(R)(C=O)N(R)(CR$_2$)$_p$—*, —OCR$_2$(C=O)—*, —OCR$_2$(C=O)(CR$_2$)$_p$—*, —OCR$_2$(C=O)O(CR$_2$)$_p$—*, —OCR$_2$(C=O)N(R)(CR$_2$)$_p$—*, —C(=O)O(CR$_2$CR$_2$O)$_n$CR$_2$CR$_2$—*, —C(=O)N(R)(CR$_2$CR$_2$O)$_n$CR$_2$CR$_2$—*, —S(CR$_2$)$_n$—*, —(CR$_2$)$_n$S—*, —(CR$_2$)$_n$SS(CR$_2$)$_p$—*, —SO$_2$(CR$_2$)$_n$—*, —(CR$_2$)$_n$SO$_2$—*, —N(R)SO$_2$(CR$_2$)$_n$—*, —(CR$_2$)$_n$SO$_2$N(R)—*, —SO$_2$N(R)(CR$_2$)$_n$—*, —(CR$_2$)$_n$N(R)SO$_2$—*, —(CR$_2$)$_n$—Ar—(CR$_2$)$_p$—*, —(CR$_2$)$_p$—Ar—(CR$_2$)$_n$—*, —O(CR$_2$)$_n$—Ar—(CR$_2$)$_p$—*, and —(CR$_2$)$_p$—Ar—(CR$_2$)$_n$O—*, wherein  indicates the position of a covalent bond with the moiety:

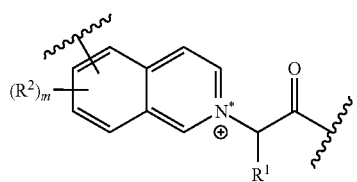

and
*** indicates the position of a covalent bond with $R^3$; each instance of n is independently a whole number selected from 1-20; each instance of p is independently an integer selected from 0-20; and R for each instance is independently selected from hydrogen, alkyl, cycloalkyl, and aryl; or two instances of R taken together with the carbons to which they are attached form a 3-6 membered carbocyclic ring; or two instances of R taken together with the atoms to which they are attached form a 5-6 membered heterocyclic ring.

In certain embodiments of the polypeptide conjugate of Formula 1, R is hydrogen and n is a whole number selected from 1-10; or R is hydrogen and n is a whole number selected from 1-10 and p is a whole number selected from 1-10. In certain embodiments of the compound of Formula 3, R is hydrogen and n is a whole number selected from 1-6; or R is hydrogen and n is a whole number selected from 1-6 and p is a whole number selected from 1-6.

The polypeptide can be a protein, enzyme, antibody, glycoprotein, or lipoprotein.

In certain embodiments, the polypeptide is hemoglobin. In certain embodiments, the hemoglobin is derived from substantially any mammalian source. Exemplary sources of hemoglobin include common livestock animals, e.g., cows, pigs, sheep and the like and humans. In certain embodiments, the hemoglobin is recombinant hemoglobin.

In certain embodiments, the polypeptide is a hemoglobin tetramer, dimer, or subunit thereof.

In certain embodiments, the hemoglobin comprises one di-alpha chain (SEQ ID NO: 4) and two beta chain (SEQ ID NO: 5) (TBN); one di-alpha chain (SEQ ID NO: 1) and two beta chain (SEQ ID NO: 2) (TBM1); or one di-alpha chain (SEQ ID NO: 1) and two beta chain (SEQ ID NO: 3) (TBM9).

In certain embodiments, the antibody is an intact antibody, single chain antibody, Fv, Fab fragment, F(ab') fragment, or F(ab')$_2$ fragment.

The methods described herein are capable of N-terminal selective conjugation of mertansine, under mild conditions (e.g., pH 6.3 at 37° C.), of the N-terminal amine by reaction of a polypeptide with a 2-ethynylbenzaldehyde analog thereby forming an N-terminal functionalized isoquinolinium with selectivity up to 99% or greater for the N-terminal amine as shown in the general reaction sequence below.

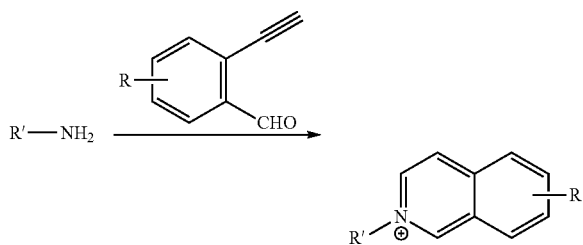

As demonstrated in the examples below, the methods described herein can afford the N-terminal functionalized polypeptide with yields of 86% or greater and moderate to excellent N-terminal selectivity (12:1 to >99:1). The resulting isoquinolonium is relatively stable and can be stored for extended periods of time without substantial degradation (See FIG. 8, which shows LCMS data for an exemplary N-terminal functionalized hemoglobin stored at 4° C. for 1-8 weeks storage). The methods described herein can thus be used as a means of selectively functionalizing a polypeptide and controlling the extent of functionalization (e.g., at least partially limiting the functionalization reaction to e.g., one per polypeptide).

By appropriate design of the 2-ethynylbenzaldehyde analog, the methods described herein can be used as a means for selectively conjugating mertansine, by covalent attachment either directly or indirectly (e.g., via a linker or linker and spacer) to the 2-ethynylbenzaldehyde analog, to the N-terminal of a polypeptide in a selective manner. As described in greater detail herein, N-terminal selective conjugation of mertansine to a polypeptide using the methods described herein can be accomplished using a one-step or two-step method.

Mertansine has the chemical structure shown below:

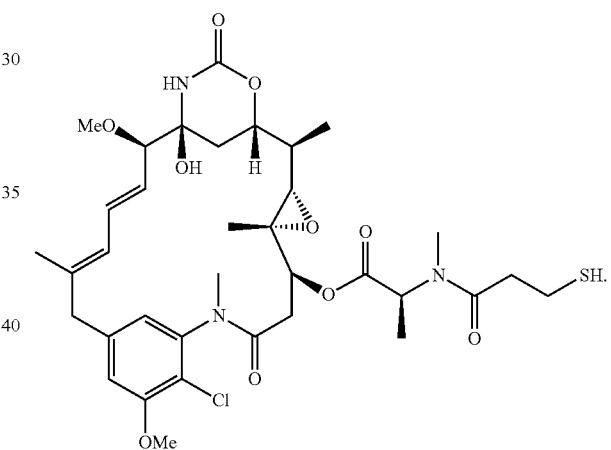

The thiol group or its conjugate base can be reacted with complimentary reactive functionality, which can be included in the 2-ethynylbenzaldehyde analog to form a covalent bond. Numerous complimentary reactive functional groups are known in the art and the selection of which is well within the skill of a person of ordinary skill in the art. Exemplary complimentary reactive functionality includes, but is not limited to, maleimides, electron deficient olefins, such as alpha-beta unsaturated esters, ketones, amides, cyanides, sulfones, sulfonamides, and imides, electron deficient alkynes, such as alkynyl esters, ketones, amides, cyanides, sulfones, and sulfonamides, alkylating agents, such as alkyl halides, tosylates, mesylates, trifluoromethylsulfates, and the like, and mercaptans.

The mertansine can be attached directly to the 2-ethynylbenzaldehyde analog or via a linker and can be conjugated to the target polypeptide using a one-step or two-step method.

The one-step method can comprise the step of: contacting a compound of Formula 3:

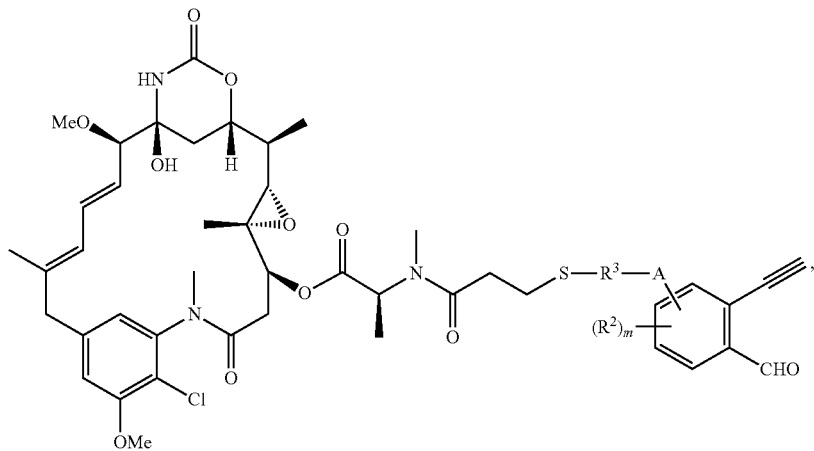

wherein A is a linker or absent;

R² independently for each instance is selected from the group consisting of hydrogen, alkyl, alkenyl, alkynyl, cycloalkyl, aryl, aralkyl, heterocycloalkyl, heteraryl, halide, cyano, nitro, hydroxyl, —OR⁴, —SR⁴, —(C=O)OR⁴, —O(C=O)R⁴, —N(R⁴)₂, —(C=O)N(R⁴)₂, —N(R⁴)(C=O)R⁴, —N(R⁴)(C=O)N(R⁴)₂, —SO₂R⁴, —N(R⁴)SO₂R⁴, and —SO₂N(R⁴)₂;

R³ is selected from the group consisting of:

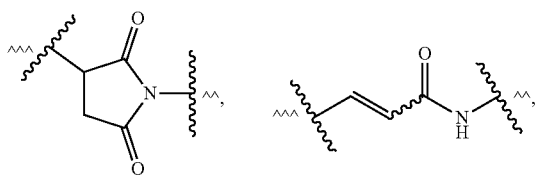

and

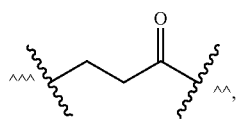 [SMILES: *CCC(*)=O]

wherein ^^ indicates the position of a covalent bond with A and ^^^ indicates the position of a covalent bond with the moiety:

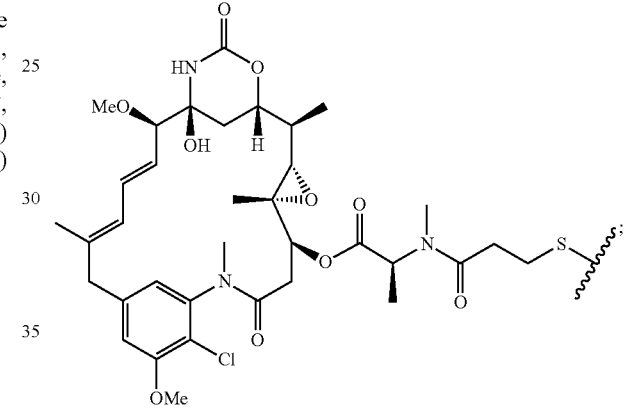

with a polypeptide comprising an N-terminal amino acid represented by the structure shown below:

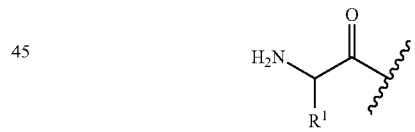

or a conjugate salt or zwitterion thereof, wherein
R¹ is the side chain of the N-terminal amino acid of the polypeptide and the N-terminal amino acid is a natural amino acid or a non-natural amino acid; thereby forming the polypeptide conjugate described herein.

In certain embodiments of the compound of Formula 3, the linker is absent or selected from the group consisting of —(CR₂)ₙ—*, —O(CR₂)ₙ—*, —(CR₂)ₙO—*, —O(CR₂)ₙO—*, —(CR₂)ₙC(=O)—*, —C(=O)(CR₂)ₙ—*, —C(=O)O(CR₂)ₙ—*, —(CR₂)ₙOC(=O)—*, —O(CR₂)ₙC(=O)—*, —O(CR₂)ₙC(=O)N(R)(CR₂)ₚ—*, —O(CR₂)ₙN(R)C(=O)N(R)(CR₂)ₚ—*, —O(CR₂)ₙC(=O)O(CR₂)ₚ—*, —O(CR₂)ₙOC(=O)N(R)(CR₂)ₚ—*, —C(=O)(CR₂)ₙO—*, —O(CR₂)ₙN(R)C(=O)—*, —O(CR₂)ₙN(R)C(=O)(CR₂)ₚ—*, —C(=O)N(R)(CR₂)ₙO—*, —OC(=O)(CR₂)ₙ—*, —(CR₂)ₙC(=O)O—*, —OC(=O)O $(CR_2)_n$—*, —$(CR_2)_n$OC(=O)O—*, —C(=O)N(R)(CR_2)_n—*, —(CR_2)_n(R)NC(=O)—*, —N(R)C(=O)(CR_2)_n—*, —(CR_2)_nC(=O)N(R)—*, —N(R)C(=O)O(CR_2)_n—*, —(CR_2)_nOC(=O)N(R)—*, —OC(=O)N(R)(CR_2)_n—*, —(CR_2)_nN(R)C(=O)O—*, —(OCR_2CR_2)_n—*, —(CR_2CR_2O)_n—*, —(OCR_2CR_2)_nOAr—*, —(OCR_2CR_2)_nAr—*, —(OCR_2CR_2)_n(C=O)—*, —(OCR_2CR_2)_nO(C=O)—*, —(OCR_2CR_2)_nN(R)(C=O)—*, —(OCR_2CR_2)_n(C=O)(CR_2)_p—*, —(OCR_2CR_2)_nO(C=O)(CR_2)_p—*, —(OCR_2CR_2)_nN(R)(C=O)(CR_2)_p—*, —(OCR_2CR_2)_n(C=O)O(CR_2)_p—*, —(OCR_2CR_2)_nO(C=O)O(CR_2)_p—*, —(OCR_2CR_2)_nN(R)(C=O)O(CR_2)_p—*, —(OCR_2CR_2)_n(C=O)N(R)(CR_2)_p—*, —(OCR_2CR_2)_nO(C=O)N(R)(CR_2)_p—*, —(OCR_2CR_2)_nN(R)(C=O)N(R)(CR_2)_p—*, —OCR_2(C=O)—*, —OCR_2(C=O)(CR_2)_p—*, —OCR_2(C=O)O(CR_2)_p—*, —OCR_2(C=O)N(R)(CR_2)_p—*, —C(=O)O(CR_2CR_2O)_nCR_2CR_2—*, —C(=O)N(R)(CR_2CR_2O)_nCR_2CR_2—*, —S(CR_2)_n—*, —(CR_2)_nS—*, —(CR_2)_nSS(CR_2)_p—*, —SO_2(CR_2)_n—*, —(CR_2)_nS 2*, —N(R)SO_2(CR_2)_n—*, —(CR_2)_nSO_2N(R)—*, —SO_2N(R)(CR_2)_n—*, —(CR_2)_nN(R)SO_2—*, —(CR_2)_n—Ar—(CR_2)_p—*, —(CR_2)_p—Ar—(CR_2)_n—*, —O(CR_2)_n—Ar—(CR_2)_p—*, and —(CR_2)_p—Ar—(CR_2)_nO—*, wherein ** indicates the position of a covalent bond with the moiety:

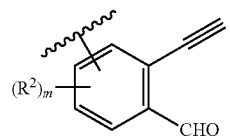

and
*** indicates the position of a covalent bond with $R^3$; each instance of n is independently a whole number selected from 1-20; each instance of p is independently an integer selected from 0-20; and R for each instance is independently selected from hydrogen, alkyl, cycloalkyl, and aryl; or two instances of R taken together with the carbons to which they are attached form a 3-6 membered carbocyclic ring; or two instances of R taken together with the atoms to which they are attached form a 5-6 membered heterocyclic ring.

In certain embodiments of the compound of Formula 3, R is hydrogen and n is a whole number selected from 1-10; or R is hydrogen and n is a whole number selected from 1-10 and p is a whole number selected from 1-10. In certain embodiments of the compound of Formula 3, R is hydrogen and n is a whole number selected from 1-6; or R is hydrogen and n is a whole number selected from 1-6 and p is a whole number selected from 1-6.

The two-step method can comprise the steps of: contacting a compound of Formula 4:

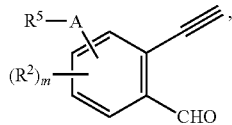

4 wherein A is a linker or is absent;
m is a whole number selected from 1-3;
$R^2$ independently for each instance is selected from the group consisting of hydrogen, alkyl, alkenyl, alkynyl, cycloalkyl, aryl, aralkyl, heterocycloalkyl, heteroaryl, halide, cyano, nitro, hydroxyl, —$OR^4$, —$SR^4$, —$(C=O)OR^4$, —$O(C=O)R^4$, —$N(R^4)_2$, —$(C=O)N(R^4)_2$, —$N(R^4)(C=O)R^4$, —$N(R^4)(C=O)N(R^4)_2$, —$SO_2R^4$, —$N(R^4)SO_2R^4$, and —$SO_2N(R^4)_2$;
$R^4$ for each instance is independently selected from the group consisting of hydrogen, alkyl, alkenyl, alkynyl, cycloalkyl, aryl, aralkyl, heterocycloalkyl, and heteroaryl; or two instances of $R^4$ taken together with the atoms to which they are attached form a 5-6 membered heterocycloalkyl; and
$R^5$ is

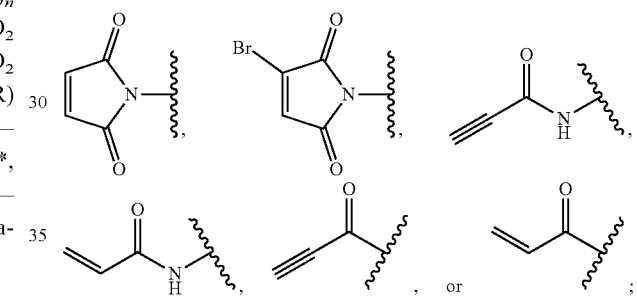

with a polypeptide comprising an N-terminal amino acid represented by the structure shown below:

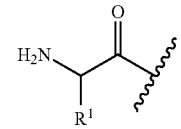

or a conjugate salt or zwitterion thereof, wherein
$R^1$ is the side chain of the N-terminal amino acid of the polypeptide and the N-terminal amino acid is a natural amino acid or a non-natural amino acid; thereby forming a functionalized polypeptide of Formula 5:

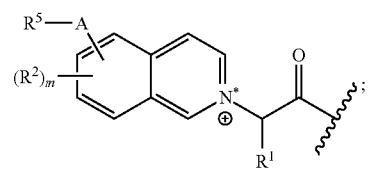

and contacting the functionalized polypeptide of Formula 5 with mertansine or a conjugate salt thereof thereby forming the polypeptide conjugate described herein.

In certain embodiments of the compound of Formula 4, the linker is absent or selected from the group consisting of —(CR$_2$)$_n$—*, —O(CR$_2$)$_n$—*, —(CR$_2$)$_n$O—*, —O(CR$_2$)$_n$O—*, —(CR$_2$)$_n$C(=O)—*, —C(=O)(CR$_2$)$_n$—*, —C(=O)O(CR$_2$)$_n$—*, —(CR$_2$)$_n$OC(=O)—*, —O(CR$_2$)$_n$C(=O)—*, —O(CR$_2$)$_n$C(=O)N(R)(CR$_2$)$_p$—*, —O(CR$_2$)$_n$N(R)C(=O)N(R)(CR$_2$)$_p$—*, —O(CR$_2$)$_n$C(=O)O(CR$_2$)$_p$—*, —O(CR$_2$)$_n$OC(=O)N(R)(CR$_2$)$_p$—*, —C(=O)(CR$_2$)$_n$O—*, —O(CR$_2$)$_n$N(R)C(=O)—*, —O(CR$_2$)$_n$N(R)C(=O)(CR$_2$)$_p$—*, —C(=O)N(R)(CR$_2$)$_n$O—*, —OC(=O)(CR$_2$)$_n$—*, —(CR$_2$)$_n$C(=O)O—*, —OC(=O)O(CR$_2$)$_n$—*, —(CR$_2$)$_n$OC(=O)O—*, —C(=O)N(R)(CR$_2$)$_n$—*, —(CR$_2$)$_n$(R)NC(=O)—*, —N(R)C(=O)(CR$_2$)$_n$—*, —(CR$_2$)$_n$C(=O)N(R)—*, —N(R)C(=O)O(CR$_2$)$_n$—*, —(CR$_2$)$_n$OC(=O)N(R)—*, —OC(=O)N(R)(CR$_2$)$_n$—*, —(CR$_2$)$_n$N(R)C(=O)O—*, —(OCR$_2$CR$_2$)$_n$—*, —(CR$_2$CR$_2$O)$_n$—*, —(OCR$_2$CR$_2$)$_n$OAr—*, —(OCR$_2$CR$_2$)$_n$Ar—*, —(OCR$_2$CR$_2$)$_n$(C=O)—*, —(OCR$_2$CR$_2$)$_n$O(C=O)—*, —(OCR$_2$CR$_2$)$_n$N(R)(C=O)—*, —(OCR$_2$CR$_2$)$_n$(C=O)(CR$_2$)$_p$—*, —(OCR$_2$CR$_2$)$_n$O(C=O)(CR$_2$)$_p$—*, —(OCR$_2$CR$_2$)$_n$N(R)(C=O)(CR$_2$)$_p$—*, —(OCR$_2$CR$_2$)$_n$(C=O)O(CR$_2$)$_p$—*, —(OCR$_2$CR$_2$)$_n$O(C=O)O(CR$_2$)$_p$—*, —(OCR$_2$CR$_2$)$_n$N(R)(C=O)O(CR$_2$)$_p$—*, —(OCR$_2$CR$_2$)$_n$(C=O)N(R)(CR$_2$)$_p$—*, —(OCR$_2$CR$_2$)$_n$O(C=O)N(R)(CR$_2$)$_p$—*, —(OCR$_2$CR$_2$)$_n$N(R)(C=O)N(R)(CR$_2$)$_p$—*, —OCR$_2$(C=O)—*, —OCR$_2$(C=O)(CR$_2$)$_p$—*, —OCR$_2$(C=O)O(CR$_2$)$_p$—*, —OCR$_2$(C=O)N(R)(CR$_2$)$_p$—*, —C(=O)O(CR$_2$CR$_2$O)$_n$CR$_2$CR$_2$—*, —C(=O)N(R)(CR$_2$CR$_2$O)$_n$CR$_2$CR$_2$—*, —S(CR$_2$)$_n$—*, —(CR$_2$)$_n$S—*, —(CR$_2$)$_n$SS(CR$_2$)$_p$—*, —SO$_2$(CR$_2$)$_n$—*, —(CR$_2$)$_n$SO$_2$—*, —N(R)SO$_2$(CR$_2$)$_n$—*, —(CR$_2$)$_n$SO$_2$N(R)—*, —SO$_2$N(R)(CR$_2$)$_n$—*, —(CR$_2$)$_n$N(R)SO$_2$—*, —(CR$_2$)$_n$—Ar—(CR$_2$)$_p$—*, —(CR$_2$)$_p$—Ar—(CR$_2$)$_n$—*, —O(CR$_2$)$_n$—Ar—(CR$_2$)$_p$—*, and —(CR$_2$)$_p$—Ar—(CR$_2$)$_n$O—*, wherein ** indicates the position of a covalent bond with the moiety:

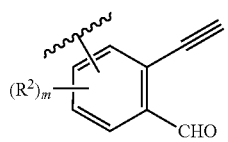

and
*** indicates the position of a covalent bond with R$^5$; each instance of n is independently a whole number selected from 1-20; each instance of p is independently an integer selected from 0-20; and R for each instance is independently selected from hydrogen, alkyl, cycloalkyl, and aryl; or two instances of R taken together with the carbons to which they are attached form a 3-6 membered carbocyclic ring; or two instances of R taken together with the atoms to which they are attached form a 5-6 membered heterocyclic ring.

In certain embodiments of the compound of Formula 4, R is hydrogen and n is a whole number selected from 1-10; or R is hydrogen and n is a whole number selected from 1-10 and p is a whole number selected from 1-10. In certain embodiments of the compound of Formula 4, R is hydrogen and n is a whole number selected from 1-6; or R is hydrogen and n is a whole number selected from 1-6 and p is a whole number selected from 1-6.

The present disclosure also provides a pharmaceutical composition comprising any one of the polypeptide conjugates described herein and at least one pharmaceutically acceptable excipient.

The polypeptide conjugates described herein and their pharmaceutically acceptable salts can be administered to a subject either alone or in combination with pharmaceutically acceptable carriers or diluents in a pharmaceutical composition according to standard pharmaceutical practice. The polypeptide conjugates can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the polypeptide conjugates described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the polypeptide conjugates described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of polypeptide conjugates of the present disclosure. These salts can be prepared in situ in the administration vehicle or the dosage form manufacturing process, or by separately reacting a purified polypeptide conjugate of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the polypeptide conjugates of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the polypeptide conjugates described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the polypeptide conjugates include the step of bringing into association a polypeptide conjugate described herein with the carrier and, optionally, one or more accessory ingredients. In general, the formulations are prepared by uniformly and intimately bringing into association a polypeptide conjugate described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more polypeptide conjugates described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the polypeptide conjugates of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

EXAMPLES

The following examples are provided by way of describing specific embodiments of this invention without intending to limit the scope of this invention in any way.

Example 1

General Procedure for Synthesis of 2-ethynylbenzaldehydes

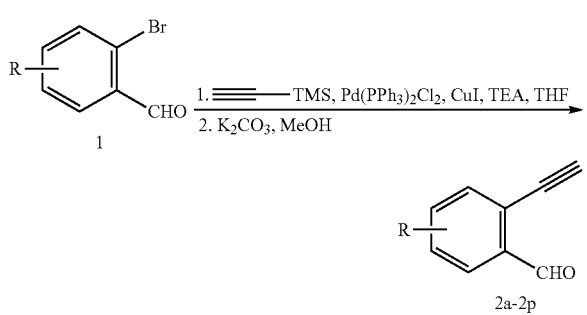

To a schlenk flask with bis(triphenylphosphine)palladium (II) dichloride (5 mol %) and copper(I) iodide (2.5 mol %) under nitrogen atmosphere, a solution of compound 1 (5 mmol) in tetrahydrofuran (50 mL) and triethylamine (0.4 M) was added at room temperature, followed by trimethylsilylacetylene (6 mmol, 1.2 equiv.), the mixture was then heated at 80-120° C. for overnight. After filtration of the mixture with celite, the filtrate was concentrated under reduced pressure and the residue was purified by column chromatography over silica gel with n-hexane/ethyl acetate (50:1) as the eluent to give reaction intermediate. The corresponding reaction intermediate was reacted with potassium carbonate (0.50 g, 3.64 mmol) in methanol (30 mL) for 30 min at room temperature, and the solvent was removed under the reduced pressure. The residue was extracted with dichloromethane and washed with saturated sodium carbonate, and dried over magnesium sulfate. The filtrate was concentrated under reduced pressure and purified by column chromatography over silica gel with n-hexane/ethyl acetate (50:1) to give 2-ethynylbenzaldehydes 2a-2p.

Example 2

N-Terminal Modification of polypeptides Using 2-ethynylbenzaldehydes 2a-2p

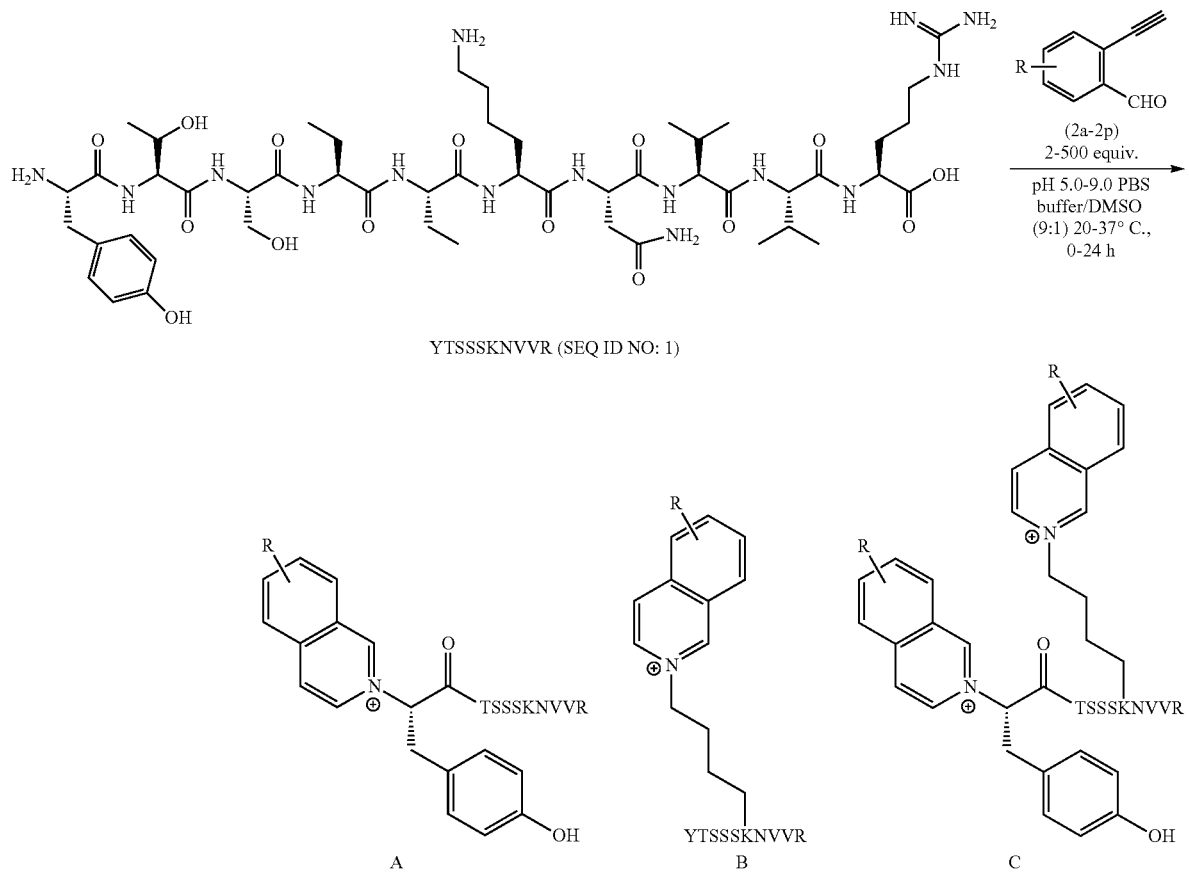

YTSSSKNVVR (SEQ ID NO: 1)

In a 1.0 mL eppendorf tube, a stock solution of polypeptides in water (1-10 mM, 10 uL), Compound 2a-2p (2-500 equivalents, 10 uL of a 2-500 mM stock solution in dimethyl sulfoxide), and phosphate-buffered saline (pH 5.0-9.0, 80 µL) are mixed. The reaction mixture is kept at 20-37° C. for 0-24 h. 10 µL of the mixture was drawn, diluted with 10 µL water and subjected to LC/MS-MS analysis to analyze the product distribution of A:B:C. Conversion and selectivity data is presented in Table 1.

TABLE 1

Results of N-Terminal modification of model peptide YTSSSKNVVR (SEQ ID NO: 1) using 2-ethynylbenzaldehyde and analogs 2a-2p.

| | | Conversion (%) | | | N-terminal selectivity of mono-modified peptide |
|---|---|---|---|---|---|
| Entry | Reagent | Mono-modified | Di-modified | Total | YTSSSKNVVR (SEQ ID NO: 1) |
| 1 | 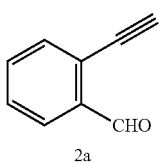 2a | 64 | 8 | (72) | 21:1 |

TABLE 1-continued
Results of N-Terminal modification of model peptide YTSSSKNVVR (SEQ ID NO: 1) using 2-ethynylbenzaldehyde and analogs 2a-2p.
| Entry | Reagent | Conversion (%) Mono-modified | Conversion (%) Di-modified | Total | N-terminal selectivity of mono-modified peptide YTSSSKNVVR (SEQ ID NO: 1) |
|---|---|---|---|---|---|
| 2 | 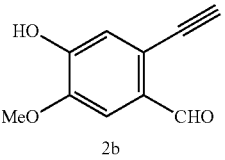 2b | 73 | 13 | (86) | >99:1 |
| 3 | 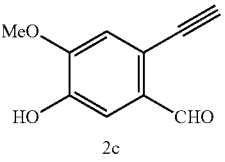 2c | 28 | 0 | (28) | 20:1 |
| 4 | 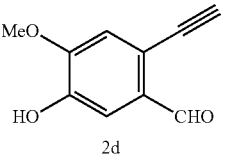 2d | 60 | 7 | (67) | 24:1 |
| 5 | 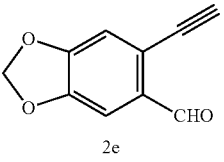 2e | 40 | 1 | (41) | 50:1 |
| 6 | 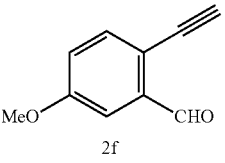 2f | 63 | 5 | (68) | 92:1 |
| 7 | 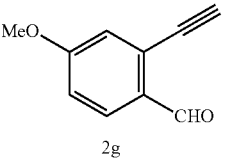 2g | 65 | 6 | (71) | 42:1 |
| 8 | 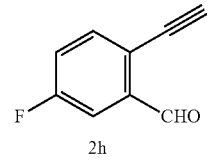 2h | 64 | 4 | (68) | 81:1 |
| 9 | 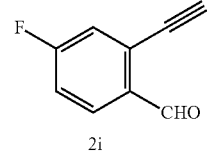 2i | 71 | 7 | (78) | 62:1 |

TABLE 1-continued
Results of N-Terminal modification of model peptide YTSSSKNVVR
(SEQ ID NO: 1) using 2-ethynylbenzaldehyde and analogs 2a-2p.
| Entry | Reagent | Conversion (%) | | | N-terminal selectivity of mono-modified peptide |
|---|---|---|---|---|---|
| | | Mono-modified | Di-modified | Total | YTSSSKNVVR (SEQ ID NO: 1) |
| 10 | 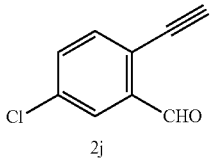 2j | 47 | 2 | (49) | 38:1 |
| 11 | 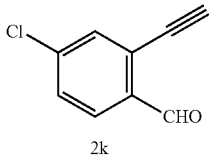 2k | 55 | 3 | (58) | 35:1 |
| 12 | 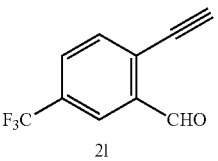 2l | 67 | 5 | (72) | 20:1 |
| 13 | 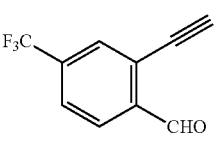 2m | 62 | 3 | (65) | 14:1 |
| 14 | 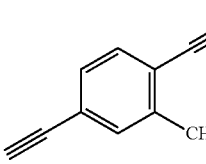 2n | 54 | 3 | (41) | 25:1 |
| 15 | 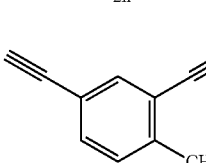 2o | 59 | 5 | (64) | 19:1 |
| 16 | 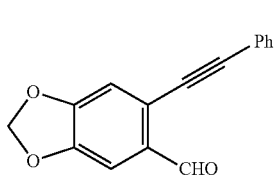 2p | 0 | 0 | (0) | — |

Example 3

Preparation of DM1 (or benzylmercaptan)-Linked 2-ethynylbenzaldehydes

To a 10 mL round bottom flask with maleimide-containing 2-ethynylbenzaldehyde (3-10 mg), a solution of DM1 (or benzylmercaptan) (1.2 equivalent) in in 500 uL of dimethyl sulfoxide or dimethylformamide was added at room temperature. The mixture was then stirred at room temperature for 5-120 min. Conversion of the reaction was monitored by analytical HPLC. The resulting product, DM1 (or benzylmercaptan)-linked 2-ethynylbenzaldehyde, was purified by an isocratic elution of acetonitrile (or methanol)-water in semi-preparative HPLC equipped with a fraction collector. Excess solvent in the collected fractions were then removed by lyophilisation to give the DM1 (or benzylmercaptan)-linked 2-ethynylbenzaldehyde.

Example 4

N-Terminal Modification of polypeptides Using DM1 (or benzylmercaptan)-Linked 2-ethynylbenzaldehyde as N-Terminal Selective Linker In a 1.0 mL Eppendorf tube, a stock solution of polypeptides in water (1-10 mM, 10 uL), DM1 (or benzylmercaptan)-linked 2-ethynylbenzaldehyde (2-500 equivalents, 10 uL of a 2-500 mM stock solution of DM1 (or benzylmercaptan)-linked 2-ethynylbenzaldehyde (in dimethyl sulfoxide), and phosphate-buffered saline (pH 5.0-9.0, 80 µL) are mixed. The reaction mixture is kept at 20-37° C. for 0-24 h. The conversion of the peptide is subjected to LC/MS and LC/MS-MS analysis to analyze the product distribution.

Example 5

Stability of 2,5-diethynylbenzaldehyde (2n)-Linked hemoglobin

Figure 8:
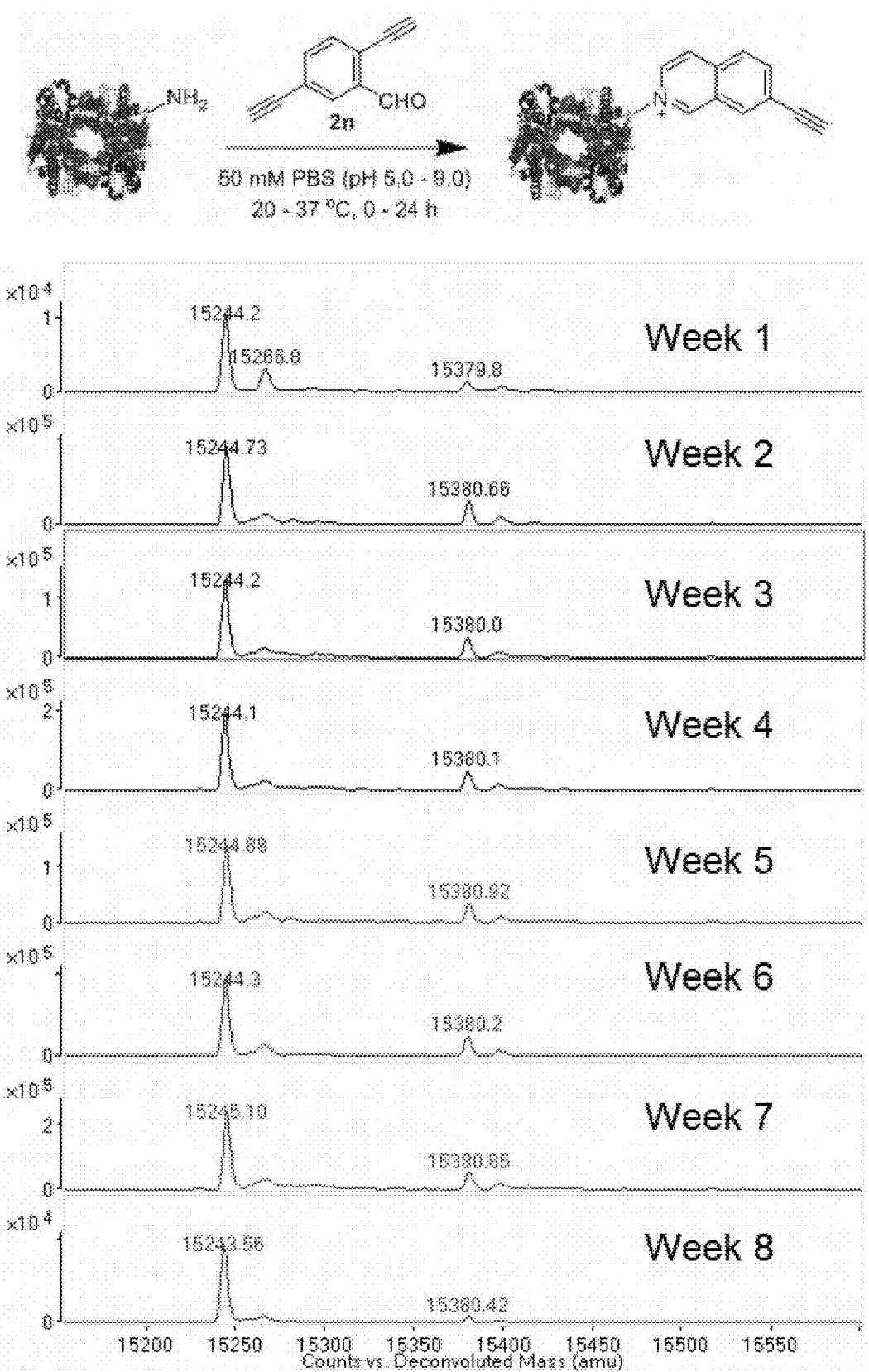
FIG. 8 shows depicts the LC-MS results of stability tests of hemoglobin N-terminal functionalized with 2,5-diethynylbenzaldehyde (2n) stored for 1-8 weeks at 4° C.

In a 1.0 mL Eppendorf tube, a stock solution of hemoglobin in water (1-10 mM, 10 uL), 2,5-diethynylbenzaldehyde (2n) (2-500 equivalents, 10 µL of a 2-500 mM stock solution of 2n in dimethyl sulfoxide), and phosphate-buffered saline (pH 5.0-9.0, 80 µL) are mixed. The reaction mixture is kept at 20-37° C. for 0-24 h. After the reaction, the modified protein was purified and stored at 4° C. refrigerator. The conversion and stability of the 2n-modified protein is subjected to LC/MS analysis on a weekly basis over a period of 8 weeks. The results are shown in FIG. 8. It indicates that the 2n-modified protein is still stable after 8 weeks.

---

What is claimed is:

1. A polypeptide conjugate represented by the structure of Formula 1:

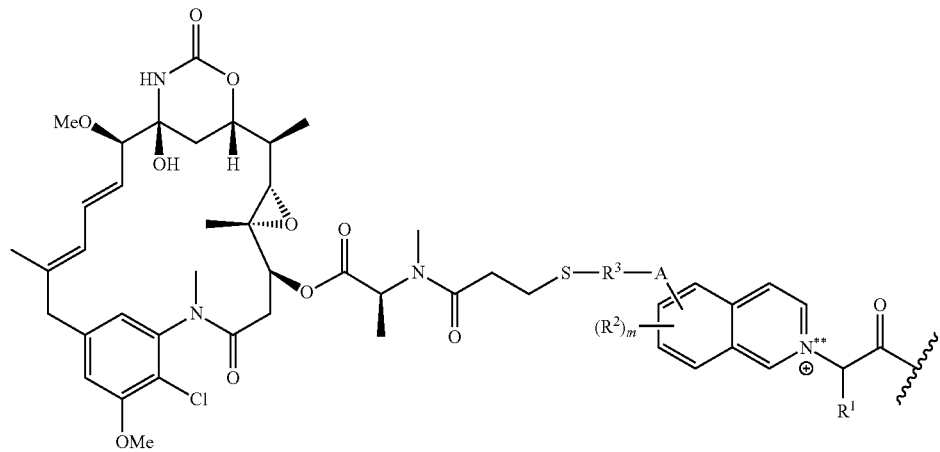

or a conjugate salt or zwitterion thereof, wherein
A is a linker or is absent;
m is a whole number selected from 1-3;

N* is the N-terminal nitrogen or Lys side chain nitrogen of the polypeptide conjugate;

$R^1$ is the side chain of the N-terminal amino acid of the polypeptide conjugate;

$R^2$ independently for each instance is selected from the group consisting of hydrogen, alkyl, alkenyl, alkynyl, cycloalkyl, aryl, aralkyl, heterocycloalkyl, heteraryl, halide, cyano, nitro, hydroxyl, —$OR^4$, —$SR^4$, —(C=O)$OR^4$, —O(C=O)$R^4$, —N($R^4$)$_2$, —(C=O)N($R^4$)$_2$, —N($R^4$)(C=O)$R^4$, —N($R^4$)(C=O)N($R^4$)$_2$, —$SO_2R^4$, —N($R^4$)$SO_2R^4$, and —$SO_2$N($R^4$)$_2$;

$R^3$ is selected from the group consisting of:

[chemical structures]

wherein ^^ indicates the position of a covalent bond with A and ^^^ indicates the position of a covalent bond with the moiety:

[chemical structure of maytansinoid derivative]

and $R^4$ for each instance is independently selected from the group consisting of hydrogen, alkyl, alkenyl, alkynyl, cycloalkyl, aryl, aralkyl, heterocycloalkyl, and heteraryl; or two instances of $R^4$ taken together with the atoms to which they are attached form a 5-6 membered heterocycloalkyl.

2. The polypeptide conjugate of claim 1, wherein the polypeptide is a protein, enzyme, antibody, glycoprotein, or lipoprotein.

3. The polypeptide conjugate of claim 2, wherein the protein is a hemoglobin protein.

4. The polypeptide conjugate of claim 3, wherein the hemoglobin protein is a hemoglobin tetramer, hemoglobin dimer, or hemoglobin monomer.

5. The polypeptide conjugate of claim 4, wherein the hemoglobin tetramer is a cross-linked hemoglobin tetramer.

6. The polypeptide conjugate of claim 1, wherein m is 1 and $R^2$ is hydrogen, —$OR^4$, or halide.

7. The polypeptide conjugate of claim 1, wherein the linker is absent or selected from the group consisting of —$(CR_2)_n$—*, —O$(CR_2)_n$—*, —$(CR_2)_n$O—*, —O$(CR_2)_n$O—*, —$(CR_2)_n$C(=O)—*, —C(=O)$(CR_2)_n$—*, —C(=O)O$(CR_2)_n$—*, —$(CR_2)_n$OC(=O)—*, —O$(CR_2)_n$C(=O)—*, —O$(CR_2)_n$C(=O)N(R)$(CR_2)_p$—*, —O$(CR_2)_n$N(R)C(=O)N(R)$(CR_2)_p$—*, —O$(CR_2)_n$C(=O)O$(CR_2)_p$—*, —O$(CR_2)_n$OC(=O)N(R)$(CR_2)_p$—*, —C(=O)$(CR_2)_n$O—*, —O$(CR_2)_n$N(R)C(=O)—*, —O$(CR_2)_n$N(R)C(=O)$(CR_2)_p$—*, —C(=O)N(R)$(CR_2)_n$O—*, —OC(=O)$(CR_2)_n$—*, —$(CR_2)_n$C(=O)O—*, —OC(=O)O$(CR_2)_n$—*, —$(CR_2)_n$OC(=O)O—*, —C(=O)N(R)$(CR_2)_n$—*, —$(CR_2)_n$(R)NC(=O)—*, —N(R)C(=O)$(CR_2)_n$—*, —$(CR_2)_n$C(=O)N(R)—*—N(R)C(=O)O$(CR_2)_n$—*, —$(CR_2)_n$OC(=O)N(R)—*, —OC(=O)N(R)$(CR_2)_n$—*, —$(CR_2)_n$N(R)C(=O)O—*, —$(OCR_2CR_2)_n$—*, —$(CR_2CR_2O)_n$—*, —$(OCR_2CR_2)_n$OAr—*, —$(OCR_2CR_2)_n$Ar—*, —$(OCR_2CR_2)_n$(C=O)—*, —$(OCR_2CR_2)_n$O(C=O)—*, —$(OCR_2CR_2)_n$N(R)(C=O)—*, —$(OCR_2CR_2)_n$(C=O)$(CR_2)_p$—*, —$(OCR_2CR_2)_n$O(C=O)$(CR_2)_p$—*, —$(OCR_2CR_2)_n$N(R)(C=O)$(CR_2)_p$—*, —$(OCR_2CR_2)_n$(C=O)O$(CR_2)_p$—*, —$(OCR_2CR_2)_n$O(C=O)O$(CR_2)_p$—*, —$(OCR_2CR_2)_n$N(R)(C=O)O$(CR_2)_p$—*, —$(OCR_2CR_2)_n$(C=O)N(R)$(CR_2)_p$—*, —$(OCR_2CR_2)_n$O(C=O)N(R)$(CR_2)_p$—*, —$(OCR_2CR_2)_n$N(R)(C=O)N(R)$(CR_2)_p$—*, —$OCR_2$(C=O)—*, —$OCR_2$(C=O)$(CR_2)_p$—*, —$OCR_2$(C=O)O$(CR_2)_p$—*, —$OCR_2$(C=O)N(R)$(CR_2)_p$—*, —C(=O)O$(CR_2CR_2O)_nCR_2CR_2$—*, —C(=O)N(R)$(CR_2CR_2O)_nCR_2CR_2$—*, —S$(CR_2)_n$—*, —$(CR_2)_n$S—*, —$(CR_2)_n$SS$(CR_2)_p$—*, —$SO_2(CR_2)_n$—*, —$(CR_2)_nSO_2$—*, —N(R)$SO_2(CR_2)_n$—*, —$(CR_2)_nSO_2$N(R)—*, —$SO_2$N(R)$(CR_2)_n$—*, —$(CR_2)_n$N(R)$SO_2$—*, —$(CR_2)_n$—Ar—$(CR_2)_p$—*, —$(CR_2)_p$—Ar—$(CR_2)_n$—*, —O$(CR_2)_n$—Ar—$(CR_2)_p$—*, and —$(CR_2)_p$—Ar—$(CR_2)_n$O—*, wherein  indicates the position of a covalent bond with the moiety:

[chemical structure with isoquinolinium ring, $(R^2)_m$ substituent, $N^*$, and $R^1$]

and

*** indicates the position of a covalent bond with $R^3$; each instance of n is independently a whole number selected from 1-20; each instance of p is independently an integer selected from 0-20; and R for each instance is independently selected from hydrogen, alkyl, cycloalkyl, and aryl; or two instances of R taken together with the carbons to which they are attached form a 3-6 membered carbocyclic ring; or two instances of R taken together with the atoms to which they are attached form a 5-6 membered heterocyclic ring.

8. The polypeptide conjugate of claim 7, wherein the linker is absent or selected from the group consisting of —$(CR_2)_n$—*, —$O(CR_2)_n$—*, —$(OCR_2CR_2)_n$—*, —$(OCR_2CR_2)_n OAr$—*, and **—$(OCR_2CR_2)_n Ar$—, wherein R is hydrogen and n is a whole number selected from 1-6.

9. The polypeptide conjugate of claim 8, wherein the polypeptide is hemoglobin.

10. The polypeptide conjugate of claim 9, wherein $R^3$ is selected from the group consisting of:

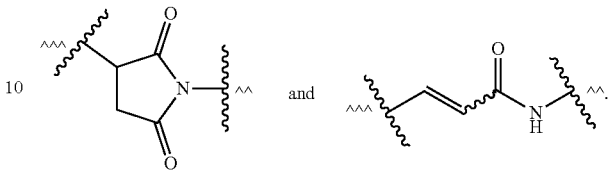

11. The polypeptide conjugate of claim 1, wherein the polypeptide conjugate is selected from the group consisting of:

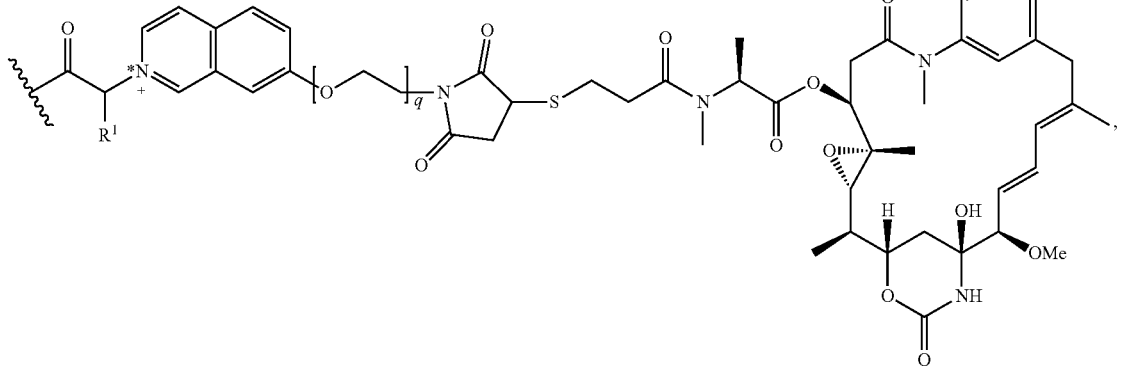

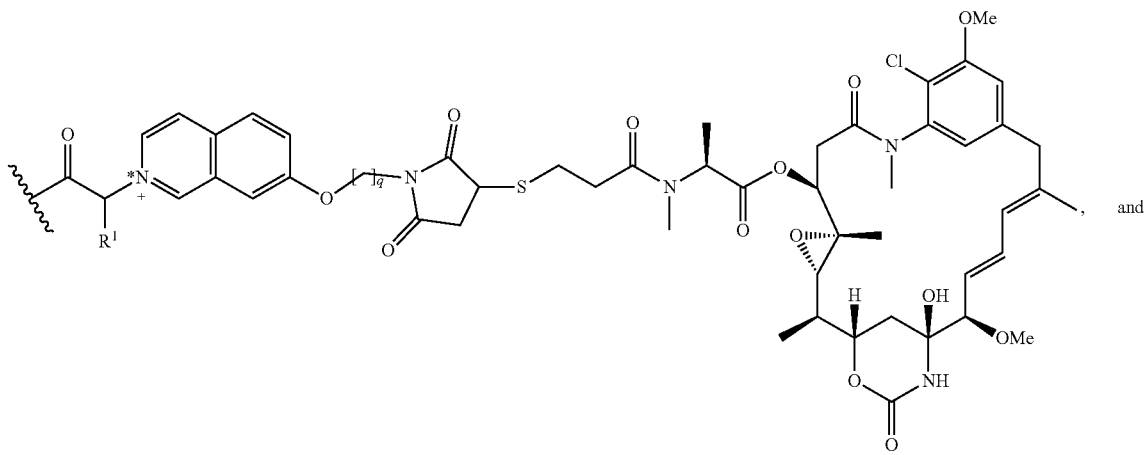

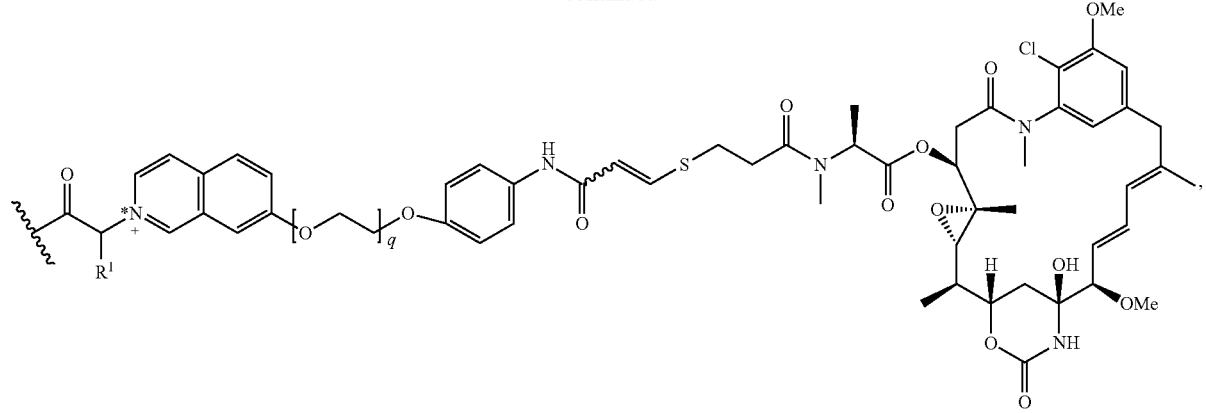
wherein q is a whole number selected from 1-10.
12. The polypeptide conjugate of claim 1, wherein the polypeptide conjugate is selected from the group consisting of:
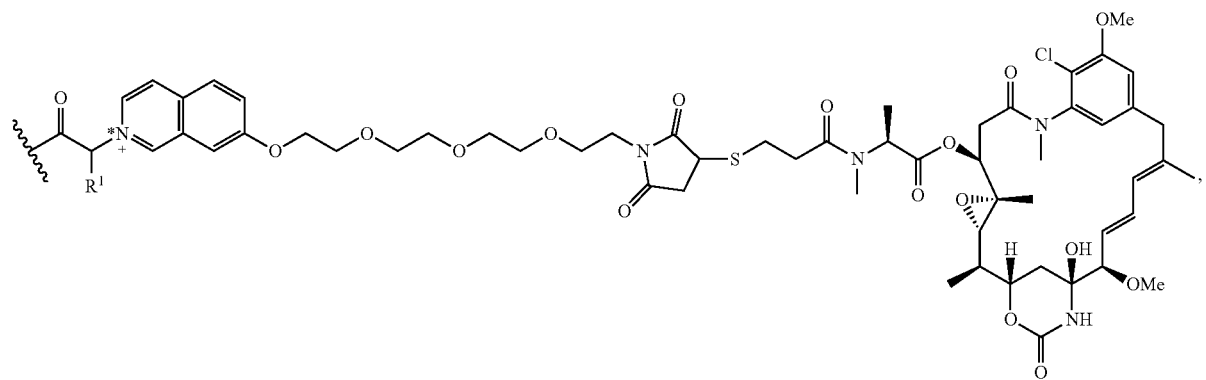
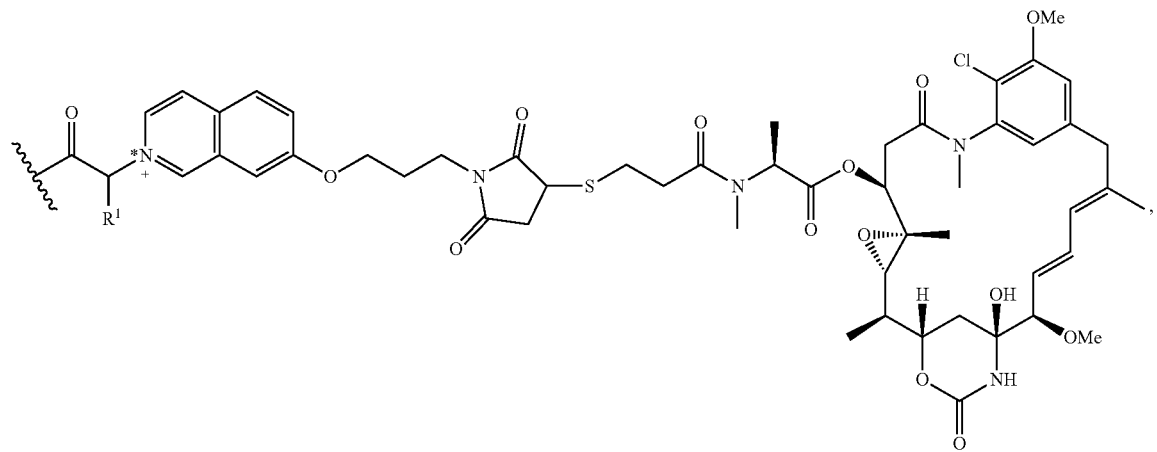

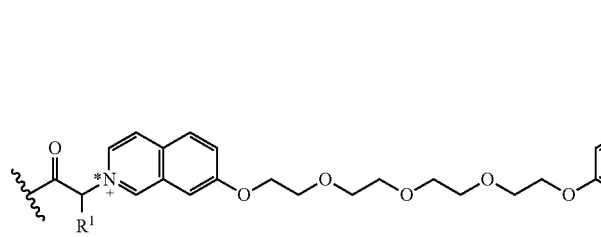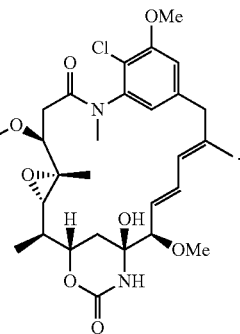

13. The polypeptide conjugate of claim 1, wherein the polypeptide comprises one or more lysine amino acids comprising a side chain represented by the structure of Formula 2:

wherein
R² independently for each instance is selected from the group consisting of hydrogen, alkyl, alkenyl, alkynyl, cycloalkyl, aryl, aralkyl, heterocycloalkyl, heteraryl,

2

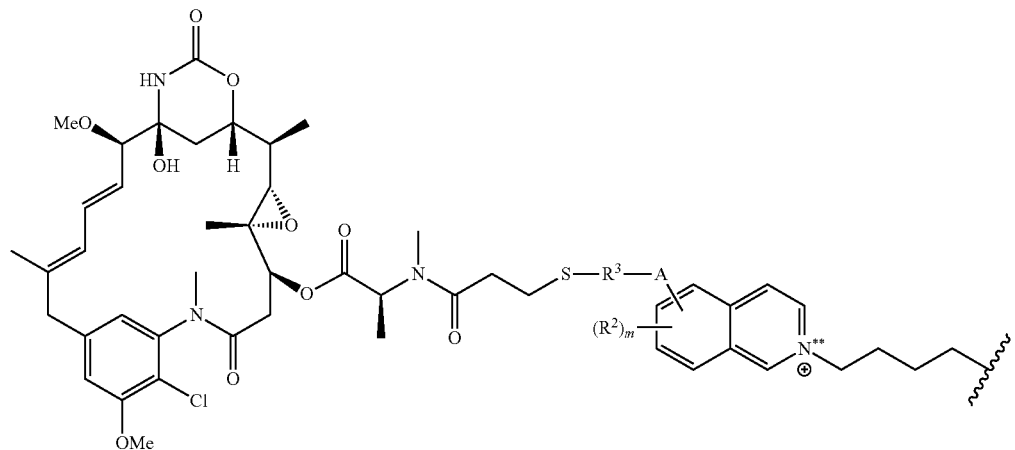

wherein N** represents the lysine side chain nitrogen.

14. A method of preparing the polypeptide conjugate of claim 1 comprising the step of contacting a compound of Formula 3:

halide, cyano, nitro, hydroxyl, —OR⁴, —SR⁴, —(C=O)OR⁴, —O(C=O)R⁴, —N(R⁴)₂, —(C=O)N(R⁴)₂, —N(R⁴)(C=O)R⁴, —N(R⁴)(C=O)N(R⁴)₂, —SO₂R⁴, —N(R⁴)SO₂R⁴, and —SO₂N(R⁴)₂;

3

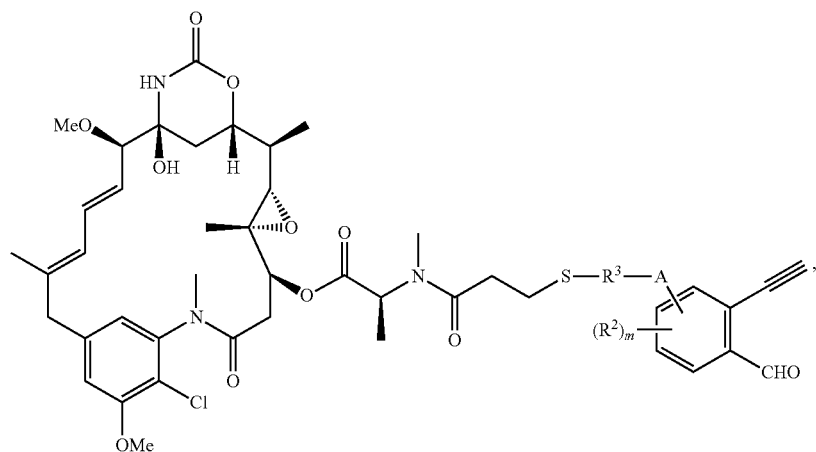

$R^3$ is selected from the group consisting of:

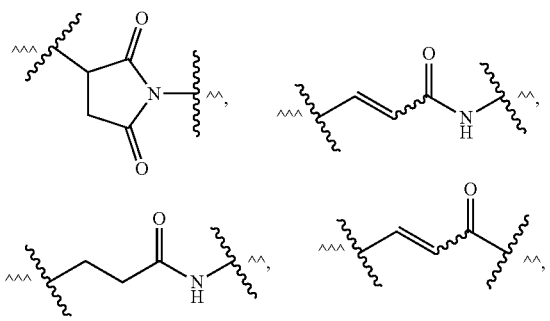

and

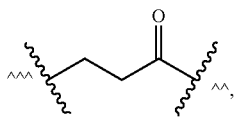

wherein ^^ indicates the position of a covalent bond with A and ^^^ indicates the position of a covalent bond with the moiety:

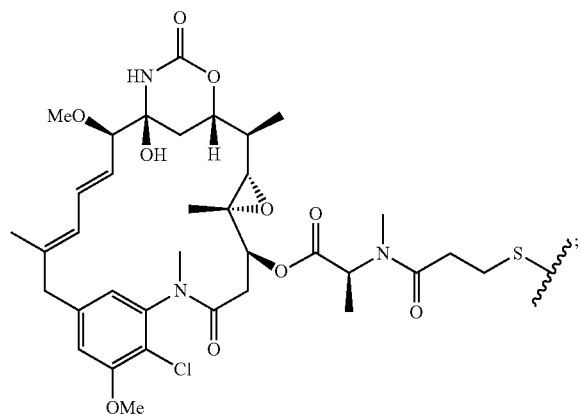

with a polypeptide comprising an N-terminal amino acid represented by the structure shown below:

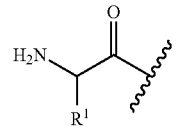

or a conjugate salt or zwitterion thereof, wherein $R^1$ is the side chain of the N-terminal amino acid of the polypeptide and the N-terminal amino acid is a natural amino acid or a non-natural amino acid; thereby forming the polypeptide conjugate of claim 1.

15. The method of claim 14, wherein $R^3$ is

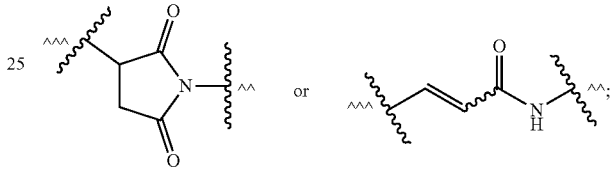

and the linker is absent or selected from the group consisting of —$(CR_2)_n$—*, —$O(CR_2)_n$—*, —$(OCR_2CR_2)_n$—*, —$(OCR_2CR_2)_n OAr$—*, and —$(OCR_2CR_2)_n Ar$—*, wherein R is hydrogen and n is a whole number selected from 1-6.

16. The method of claim 14, wherein the polypeptide is hemoglobin.

17. A pharmaceutical composition comprising the polypeptide conjugate of claim 1 and at least one pharmaceutically acceptable excipient.

* * * * *

SEQUENCE LISTING

```
<160> NUMBER OF SEQ ID NOS: 5

<210> SEQ ID NO 1
<211> LENGTH: 283
<212> TYPE: PRT
<213> ORGANISM: Artificial Sequence
<220> FEATURE:
<223> OTHER INFORMATION: Artificial sequence prepared in the lab

<400> SEQUENCE: 1

Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Phe Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly Gln Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg Gly Met Leu
    130                 135                 140

Ser Pro Ala Asp Lys Thr Asn Val Lys Ala Ala Trp Gly Lys Val Gly
145                 150                 155                 160

Ala His Ala Gly Glu Tyr Gly Ala Glu Ala Phe Glu Arg Met Phe Leu
                165                 170                 175
```

```
Ser Phe Pro Thr Thr Lys Thr Tyr Phe Pro His Phe Asp Leu Ser His
            180                 185                 190

Gly Ser Ala Gln Val Lys Gly Gln Gly Lys Val Ala Asp Ala Leu
            195                 200             205

Thr Asn Ala Val Ala His Val Asp Asp Met Pro Asn Ala Leu Ser Ala
            210                 215                 220

Leu Ser Asp Leu His Ala His Lys Leu Arg Val Asp Pro Val Asn Phe
225                 230                 235                 240

Lys Leu Leu Ser His Cys Leu Leu Val Thr Leu Ala Ala His Leu Pro
                245                 250                 255

Ala Glu Phe Thr Pro Ala Val His Ala Ser Leu Asp Lys Phe Leu Ala
            260                 265                 270

Ser Val Ser Thr Val Leu Thr Ser Lys Tyr Arg
            275                 280

<210> SEQ ID NO 2
<211> LENGTH: 146
<212> TYPE: PRT
<213> ORGANISM: Artificial Sequence
<220> FEATURE:
<223> OTHER INFORMATION: Artificial sequence prepared in the lab

<400> SEQUENCE: 2

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3
<211> LENGTH: 146
<212> TYPE: PRT
<213> ORGANISM: Artificial Sequence
<220> FEATURE:
<223> OTHER INFORMATION: Artificial sequence prepared in the lab

<400> SEQUENCE: 3

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45
```

Ser Thr Pro Asp Ala Val Met Gly Asn Pro Lys Val Lys Ala His Gly
    50                  55                  60

Lys Val Leu Gly Ala Phe Ser Asp Gly Leu Ala His Leu Asp Asn
65              70                  75                  80

Leu Asp Gly Thr Phe Ala Thr Leu Ser Glu Leu His Cys Asp Lys Leu
                85                  90                  95

His Val Asp Pro Glu Asn Phe Arg Leu Leu Gly Lys Val Leu Val Cys
            100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
            130                 135                 140

Tyr His
145

<210> SEQ ID NO 4
<211> LENGTH: 283
<212> TYPE: PRT
<213> ORGANISM: Artificial Sequence
<220> FEATURE:
<223> OTHER INFORMATION: Artificial sequence prepared in the lab

<400> SEQUENCE: 4

Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65              70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg Gly Met Leu
            130                 135                 140

Ser Pro Ala Asp Lys Thr Asn Val Lys Ala Ala Trp Gly Lys Val Gly
145                 150                 155                 160

Ala His Ala Gly Glu Tyr Gly Ala Glu Ala Leu Glu Arg Met Phe Leu
            165                 170                 175

Ser Phe Pro Thr Thr Lys Thr Tyr Phe Pro His Phe Asp Leu Ser His
            180                 185                 190

Gly Ser Ala Gln Val Lys Gly His Gly Lys Lys Val Ala Asp Ala Leu
            195                 200                 205

Thr Asn Ala Val Ala His Val Asp Asp Met Pro Asn Ala Leu Ser Ala
            210                 215                 220

Leu Ser Asp Leu His Ala His Lys Leu Arg Val Asp Pro Val Asn Phe
225                 230                 235                 240

Lys Leu Leu Ser His Cys Leu Leu Val Thr Leu Ala Ala His Leu Pro
                245                 250                 255

```
Ala Glu Phe Thr Pro Ala Val His Ala Ser Leu Asp Lys Phe Leu Ala
            260                 265                 270

Ser Val Ser Thr Val Leu Thr Ser Lys Tyr Arg
            275                 280

<210> SEQ ID NO 5
<211> LENGTH: 146
<212> TYPE: PRT
<213> ORGANISM: Artificial Sequence
<220> FEATURE:
<223> OTHER INFORMATION: Artificial sequence prepared in the lab

<400> SEQUENCE: 5

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
        50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
        130                 135                 140

Tyr His
145
```